(12) United States Patent
Chaplin et al.

(10) Patent No.: US 8,877,967 B2
(45) Date of Patent: Nov. 4, 2014

(54) COMPOSITIONS AND METHODS FOR INHIBITION OF CATHEPSINS

(71) Applicants: OXiGENE, Inc., South San Francisco, CA (US); Baylor University, Waco, TX (US)

(72) Inventors: David J. Chaplin, Watlington (GB); Kishore Kumar Gaddale Devanna, Glasgow (GB); Erica Parker, Waco, TX (US); Kevin G. Pinney, Woodway, TX (US); Jiangli Song, Waco, TX (US); Mary Lynn Trawick, Woodway, TX (US)

(73) Assignees: OXiGENE, Inc., South San Francisco, CA (US); Baylor University, Waco, TX (US)

( * ) Notice: Subject to any disclaimer, the term of this patent is extended or adjusted under 35 U.S.C. 154(b) by 0 days.

(21) Appl. No.: 13/786,142

(22) Filed: Mar. 5, 2013

(65) Prior Publication Data
US 2013/0296605 A1 Nov. 7, 2013

Related U.S. Application Data

(60) Provisional application No. 61/615,091, filed on Mar. 23, 2012.

(51) Int. Cl.
*C07C 337/08* (2006.01)
(52) U.S. Cl.
CPC .................................. *C07C 337/08* (2013.01)
USPC .............................................. 564/20; 564/21
(58) Field of Classification Search
CPC ...................................................... C07C 337/08
USPC ....................................................... 564/20, 21
See application file for complete search history.

(56) References Cited

U.S. PATENT DOCUMENTS

| 6,897,240 | B2 | 5/2005 | Cohen et al. |
| 8,173,696 | B2 | 5/2012 | Siles et al. |
| 2004/0014801 | A1 | 1/2004 | Cohen et al. |
| 2005/0182121 | A1 | 8/2005 | Cohen et al. |
| 2011/0305632 | A1 | 12/2011 | Donnelly et al. |

FOREIGN PATENT DOCUMENTS

WO 2005/087211 A1 9/2005

OTHER PUBLICATIONS

CAS Registry™, CAS No. 882815-61-4, entered May 4, 2006.*
Benassi and Taddei, "Theoretical investigations of the structural and chemical properties of hydrazinecarboxamide and hydrazinecarbothioamide." Journal of Molecular Structure (Theochem). 1988, vol. 164, pp. 275-288.

Chavarria, et al., "Initial evaluation of the antitumor activityof KGP94, a functionalized benzophenone thiosemicarbazone inhibitor of cathepsin L." 2012, vol. 58, pp. 568-572.
Chiyanzu, et al., "Synthesis and evaluation of isatins and thiosemicarbazone derivatives against cruzain, falcipain-2 and rhodesain." 2003, vol. 13, pp. 3527-3530.
Du, et al., "Synthesis and structure-activity relationship study of potent trypanocidal thio semicarbazone inhibitors of the trypanosomal cysteine protease cruzain." 2002, vol. 45, pp. 2695-2707.
Fujii, et al., "discovery of potent thiosemicarbzone inhibitors of rhodesain and cruzain." Bioorg. Med. Chem. Lett. 2005, vol. 15, pp. 121-123.
Gocheva and Joyce, "Cysteine cathepsins and the cutting edge of cancer invasion." Cell Cycle. 2007, vol. 6, pp. 60-64.
Greenbaum, et al., "Synthesis and structure-activity relationships of parasitical thiosemicarbazone cysteine protease inhibitors against *Plasmodium falciparum, Trypanosoma brucei*, and *Trypanosoma cruzi*." J. Med. Chem. 2004, vol. 47, pp. 3212-3219.
Kishore Kumar, et al., "Design, synthesis, and biological evaluation of potent thiosemicarbazone based cathepsin L inhibitors." Bioorg. Med. Chem. Lett. 2010, vol. 20, pp. 1415-1419.
Kishore Kumar, et al., "Functionalized benzophenone, thiophenone, pyridine, and fluorene thiosemicarbazone derivatives as inhibitors of cathepsin L." Bioorg. Med. Chem. Lett. 2010, vol. 20, pp. 6610-6615.
Mallari, et al., "Discovery of trypanocidal thiosemicarbazone inhibitors of rhodesain and TbcatB." Bioorg. Med. Chem. Lett. 2008, vol. 18, pp. 2883-2885.
Pizzo, et al. "Selenosemicarbazones as potent cruzipain inhibitors and their antiparasitic properties against *Trypanosoma cruzi*." Med. Chem. Commun. Available on-line Dec. 7, 2011, DOI: 10.1039/c2md00283c.
Shah, et al., "A small-molecule oxocarbazate inhibitor of human cathepsin L blocks severe acute respiratory syndrome and ebola pseudotype virus infection into human embryonic kidney 293T cells." Molecular Pharmacology. 2010, vol. 78, pp. 319-324.

(Continued)

*Primary Examiner* — Paul A Zucker
*Assistant Examiner* — Mark Luderer
(74) *Attorney, Agent, or Firm* — Karen E. Flick

(57) ABSTRACT

This invention is directed to compound of Formula I and methods of using these compounds in the treatment of conditions in which modulation of a cathepsin, particularly cathepsin K or cathepsin L, will be therapeutically useful.

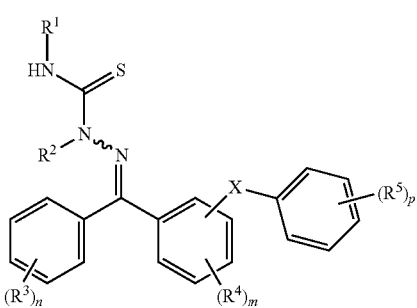

20 Claims, No Drawings

(56) References Cited

OTHER PUBLICATIONS

Siles, et al., "Design, synthesis, and biochemical evaluation of novel cruzain inhibitors with potential application in the treatment of Chagas' disease." Bioorg. Med. Chem. Lett. 2006, vol. 16, pp. 4405-4409.

Song, et al. "Synthesis and biochemical evaluation of thiochromanone thiosemicarbazone analogues of inhibitors of cathepsin L." Med. Chem. Lett. 2012, vol. 3, pp. 450-453.

Song, et al. "Small-molecule inhibitors of cathepsin L incorporating functionalized ring-fused molecular frameworks." Bioorg. & Med. Chem. Lett. 2013 (available on-line Dec. 20, 2012), vol. 23, pp. 2801-2807.

Amin and Amin, "Fries Rearrangement of esters of 2-methyl-4-benzoylphenol" J. Indian Chem. Soc. 1960, vol. 37, pp. 469-72.

Rogelio Siles, Dissertation entitled: "Design, Synthesis and Biological Evaluation of New Anti-Cancer Nitrogen-Containing Combretastatins and Novel Cysteine Protease Inhibitors for the Treatment of Chagas Disease." Submitted to Baylor University, Dec. 2005.

Wara Milenka Arispe Angulo, Dissertation entitled: "Inhibitors of Human Cathepsin L and Cruzain as Therapeutic Agents." Submitted to Baylor Univeristy, Dec. 2008.

Shen-En Chen, Dissertation entitled: Modeling, Design, and Development of Potential Inhibitors of γ-Glutamylamine Cyclotransferase and Inhibitors of Cruzain as Therapeutic Agent for Chagas' Disease Submitted to Baylor Univeristy, May 2008.

\* cited by examiner

COMPOSITIONS AND METHODS FOR INHIBITION OF CATHEPSINS

I. CROSS-REFERENCE TO RELATED APPLICATIONS

This application claims the benefit of U.S. provisional patent application No. 61/615,097, filed on 23 Mar. 2012, which application is incorporated herein by reference in its entirety.

II. INTRODUCTION

A. Field

The present invention relates to compounds and methods of using these compounds in the treatment of conditions in which modulation of the cathepsin, particularly cathepsin K or cathepsin L, is therapeutically useful.

B. Background

There are five classes of proteases including matrix metalloproteases (MMPs), cysteine proteases, serine proteases, aspartic proteases, and threonine proteases which catalyze the hydrolysis of peptide bonds. Due to their function in many disease states, including cancer and cardiovascular disease, proteases have become well-investigated therapeutic targets. Upregulation of MMPs is associated with cancer metastasis, consequently much research has been done to inhibit their activity. Since inhibitors of MMPs have failed to progress beyond clinical trials, interest in the other classes of proteases as therapeutic targets has grown significantly.

Cysteine protease cathepsins, members of the papain family, have recently been validated as an important enzymatic class to target in cancer research. In this family, there are eleven cathepsin enzymes known to date in humans: B, C, F, H, K, L, O, S, V, W, and X. Cathepsins are found in the highest concentration in cellular lysosomes, and during cancer progression they are secreted at an increased rate and degrade the extracellular matrix and basement membrane, which aid in cancer metastasis. Cathepsins B and L have been investigated extensively, due to their increased expression and activity in human and mouse tumors. Cathepsin K has also been the target of much research, due to its role in bone resorption and implications in osteoporosis. Odanacatib, an inhibitor of cathepsin K developed by Merck, is currently in phase III clinical trials for the treatment of osteoporosis.

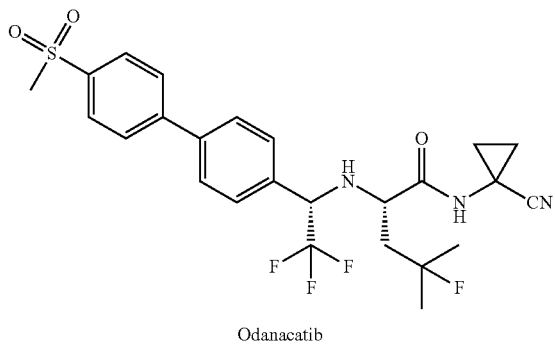 [SMILES: CC(C)(F)C[C@H](N[C@@H](c1ccc(-c2ccc(S(C)(=O)=O)cc2)cc1)C(F)(F)F)C(=O)NC1(C#N)CC1]

Odanacatib

Cathepsin L also has a major function in intracellular lysosomal proteolysis, and in the degradation of the extracellular matrix (ECM) during the growth and metastasis of primary tumors. Despite the importance of cathepsin L in cancer metastasis and considerable interest in the enzyme as a target for synthesis of new potential anticancer agents, there are no clinical trials testing inhibitors of cathepsin L in cancer metastasis. This is in contrast to the application of odanacatib to prevent bone loss in osteoporosis and cancer that has metastasized to bone. Odanacatib is a specific inhibitor of cathepsin K, an enzyme that is involved in degradation of the extracellular matrix proteins associated with bone resorption. Cathepsin K is a distinct enzyme in structure and function from that of cathepsin L. Small molecule inhibitors of cathepsin L have been previously identified, including azapenone (I), a cyanamide derivative (II), and a purine nitrile analogue (III), as well as amino acid based molecules including an epoxide derivative (IV) and an oxocarbazate analogue (V).

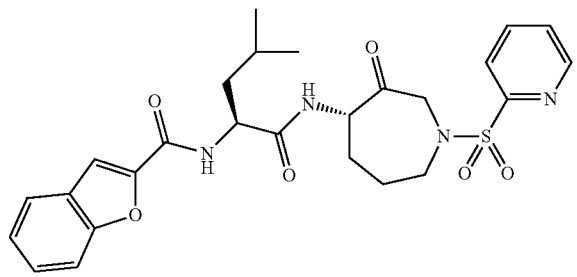

(I)

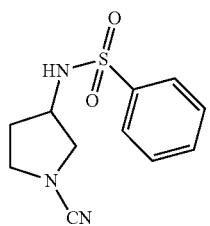

(II)

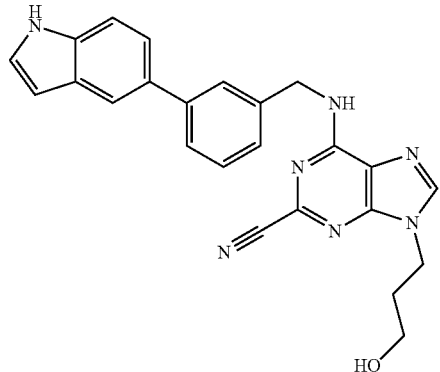

(III)

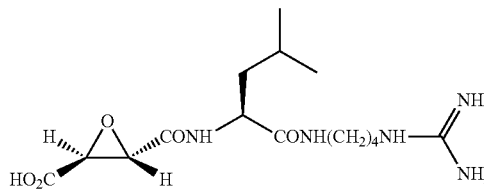

(IV)

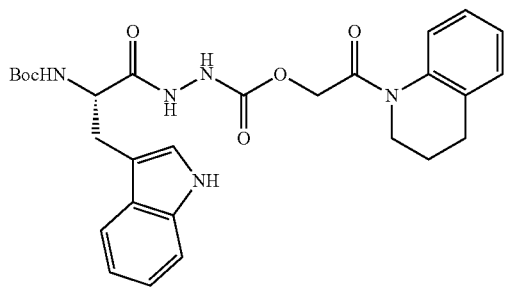

(V)

Cathepsin L also has been implicated in regulatory events relating to diabetes, immunological responses, degradation of the articular cartilage matrix, and other pathological processes (Chapman et al., 1997, *Annu Rev Physiol* 59:63-88; Turk and Guncar, 2003 *Acta Crystallogr D Biol Crystallogr* 59:203-213; Maehr et al., 2005, *J Clin Invest* 115:2934-2943; Vasiljeva et al., 2007, *Curr Pharm Des* 13:387-403), including osteoporosis and rheumatoid arthritis, (McGrath, 1999 *Annu Rev Biophys Biomol Struct* 28:181-204; Turk et al., 2001 *EMBO J* 20:4629-4633; Potts et al., 2004 *Int J Exp Pathol* 85:85-96; Schedel et al., 2004 *Gene Ther* 11:1040-1047). Further, inhibition of cathepsin L has also been shown to block Severe Acute Respiratory Syndrome (SARS) and Ebola pseudotype virus infection (Shah et al., 2010, *Molecular Pharmacology* 78(2):319-324).

In view of the important role of cathepsins in mediating a variety of disease, there is an urgent need to develop potent, efficacious and pharmaceutically acceptable compounds capabe of inhibiting the activity of cathepsins L and K.

III. SUMMARY OF THE INVENTION

This invention is directed to compounds and methods of using these compounds in the treatment of conditions in which modulation of a cathepsin, particularly cathepsin K or cathepsin L, will be therapeutically useful.

One aspect provides a compound of formula I:

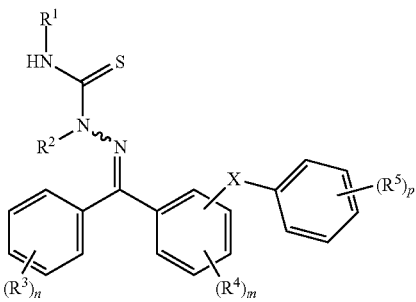

wherein
X is selected from the group consisting of C(=O), CH(OR$^6$) and

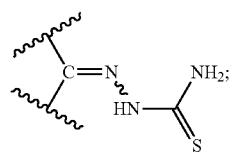 [SMILES: *C(*)=NNC(N)=S]

n is 0, 1, 2 or 3;
m is 0, 1, 2 or 3;
p is 0, 1, 2 or 3;
R$^1$ is hydrogen, C$_1$-C$_3$ alkyl, aryl or arylalkyl;
R$^2$ is hydrogen or C$_1$-C$_3$ alkyl;
each R$^3$ and R$^5$ independently is selected from the group consisting of hydroxyl, C$_1$-C$_3$ alkyl, C$_1$-C$_2$ alkoxy, fluoro, and chloro;
each R$^4$ independently is selected from the group consisting of hydroxyl, C$_1$-C$_6$ alkyl, C$_1$-C$_6$ alkoxy, halo, amino, nitro, nitroso, and acyl; and
R$^6$ is selected from the group consisting of hydrogen and methyl.

In certain implementations, the invention provides compounds of formula II:

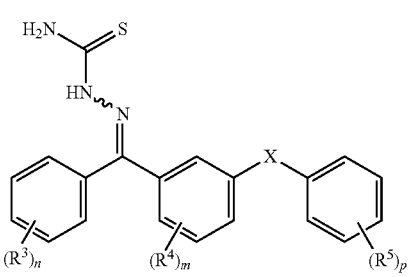

wherein X, R$^3$, R$^4$, R$^5$, n, m and p are as defined above.
In other implementations, the invention provides compounds of formula III:

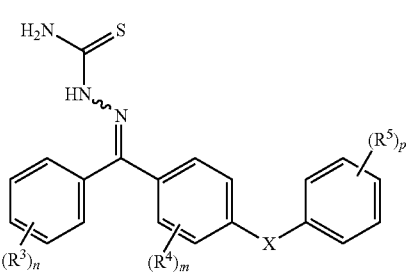

wherein X, R$^3$, R$^4$, R$^5$, n, m and p are as defined above.
In one implementation, the present invention provides a compound of formula I or formula II, a solvate, or pharmaceutically acceptable salt thereof.

In another implementation, this invention provides a method of inhibiting an activity of a cathepsin, comprising contacting the cathepsin with an amount of a compound of Formula I effective to inhibit an activity of the cathepsin.

In another implementation, this invention provides a method of inhibiting an activity of a cathepsin, comprising contacting in vitro a cathepsin K or cathepsin L with an amount of a compound of this invention to inhibit an activity of the cathepsin.

In another implementation, this invention provides a method of inhibiting an activity of a cathepsin, comprising contacting in a cell a cathepsin with an amount of a compound effective to inhibit an activity of the cathepsin wherein the compound is selected from the compounds of this invention, as described above.

In another implementation, this invention provides a method of inhibiting a neoplasm, comprising administering to a patient suffering from such neoplasm an amount of a compound of this invention effective to treat the neoplasm. In other implementations, the compounds described herein can be used to treat non-neoplastic conditions such as osteoporosis, viral infections and parasites, particularly protozoal parasites. In one aspect, the present invention provides a method for inhibiting a cysteine protease involved in the infectious life cycle of a protozoan parasite, the method comprising the step of administering to the subject a compound described herein, said compound administered to the subject in an amount sufficient to disrupt the infectious life cycle of a protozoan parasite. Exemplary protozoan cysteine proteases include those required in the infectious life cycle of a trypanosome, such as cruzain or cruzipain from *T. cruzi*, rhodesain or brucipain from *T. brucei rhodesiense*, and congopain from *T. congolense*; a plasmodium, such as falcipain from *P. falciparum*; or a leishmania, such as CPB2.8 Delta CTE from *L. mexicana*.

In another implementation, this invention provides a pharmaceutical formulation comprising a thiosemicarbazone as described above.

In another implementation, this invention provides a kit comprising a thiosemicarbazone as described above, packaging, and instructions for use.

It will be appreciated by one of skill in the art that the implementations summarized above may be used together in any suitable combination to generate implementations not expressly recited above and that such implementations are considered to be part of the present invention.

IV. DETAILED DESCRIPTION

The invention encompasses compounds having formula I and the compositions and methods using these compounds in the treatment of conditions in which modulation of a cathepsin, particularly cathepsin K or cathepsin L, is therapeutically useful.

As used herein, the following definitions shall apply unless otherwise indicated.

"Alkyl" refers to monovalent saturated aliphatic hydrocarbon groups having from 1 to 10 carbon atoms and preferably 1 to 6 carbon atoms. This term includes, by way of example, linear and branched hydrocarbon groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Amino" refers to the group —$NH_2$.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like), provided that the point of attachment is through an atom of the aromatic aryl group. Preferred aryl groups include phenyl and naphthyl.

"Alkenyl" refers to straight chain or branched hydrocarbon groups having from 2 to 6 carbon atoms and preferably 2 to 4 carbon atoms and having at least 1 and preferably from 1 to 2 sites of double bond unsaturation. Such groups are exemplified, for example, bi-vinyl, allyl, and but-3-en-1-yl. Included within this term are the cis and trans isomers or mixtures of these isomers.

"Alkynyl" refers to straight or branched monovalent hydrocarbon groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—$CH_2$C≡CH).

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like.

"Halo" or "halogen" refers to fluoro, chloro, bromo, and iodo and is preferably fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen, and sulfur within the ring. Such heteroaryl groups can have a single ring (e.g., pyridinyl, imidazolyl or furyl) or multiple condensed rings (e.g., indolizinyl, quinolinyl, benzimidazolyl or benzothienyl), wherein the condensed rings may or may not be aromatic and/or contain a heteroatom, provided that the point of attachment is through an atom of the aromatic heteroaryl group. In one implementation, the nitrogen and/or sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In one implementation, the nitrogen and/or sulfur atom(s) of the heterocyclic group are optionally oxidized to provide for the N-oxide, —S(O)—, or —$SO_2$— moieties.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Nitro" refers to the group —$NO_2$.

"Nitroso" refers to the group —NO.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

The term "substituted," when used to modify a specified group or radical, means that one or more hydrogen atoms of the specified group or radical are each, independently of one another, replaced with the same or different substituent groups as defined below.

Substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)R$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{\lambda}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means e.g. that one of the counter ions for such divalent alkali earth ions can be an ionized form of a compound of the invention and the other a typical counter ion such as chloride, or two ionized compounds of the invention can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In a preferred implementation, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to -substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

"Patient" refers to human and non-human animals, especially mammals.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders and neoplasms, a pharmaceutically or therapeutically effective amount comprises an amount sufficient to, among other things, cause the tumor to shrink or decrease the growth rate of the tumor.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water.

Similarly, it is understood that the above definitions are not intended to include impermissible substitution patterns (e.g., methyl substituted with 5 fluoro groups). Such impermissible substitution patterns are easily recognized by a person having ordinary skill in the art.

This invention provides novel thiosemicarbazone compounds and methods of making the compound and methods of using these compounds in the treatment of conditions in which inhibition of a cathepsin, particularly cathepsin K and/or cathepsin L, is therapeutically useful. These conditions include, but are not limited to, neoplasms, osteoporosis, protozoal parasite infection and viral infections. Given the severity of and suffering caused by these conditions, it is vital that new treatments are developed to treat these conditions.

In one implementation, the present invention provides a compound of formula I, solvates, or pharmaceutically acceptable salts thereof.

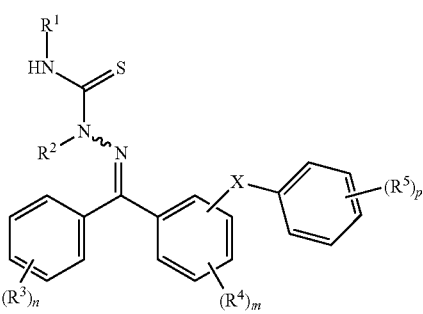

I wherein

X is selected from the group consisting of C(=O), CH(OR$^6$) and

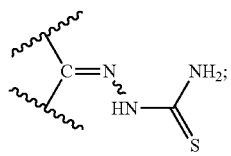 [SMILES: *C(*)=NNC(N)=S]

n is 0, 1, 2 or 3;
m is 0, 1, 2 or 3;
p is 0, 1, 2 or 3;
$R^1$ is hydrogen, $C_1$-$C_3$ alkyl, aryl or arylalkyl;
$R^2$ is hydrogen or $C_1$-$C_3$ alkyl;
each $R^3$ and $R^5$ independently is selected from the group consisting of hydroxyl, $C_1$-$C_3$ alkyl, $C_1$-$C_2$ alkoxy, fluoro, and chloro;
each $R^4$ independently is selected from the group consisting of hydroxyl, $C_1$-$C_6$ alkyl, $C_1$-$C_6$ alkoxy, halo, amino, nitro, nitroso and acyl; and
$R^6$ is selected from the group consisting of hydrogen and methyl.

Preferably, n, m and p independently are zero or one. In some implementations, $R^1$ and $R^2$ independently are hydrogen or methyl. In certain implementations, both $R^1$ and $R^2$ are hydrogen. In other implementations, n is one and $R^3$ is selected from the group consisting of hydroxyl, methyl, methoxy, and fluoro. In alternative implementations, p is one and $R^5$ is selected from the group consisting of hydroxyl, methyl, methoxy and fluoro. In yet other implementations, m is one and $R^4$ is selected from the group consisting of halo and acyl.

In other implementations, X is C(=O) or CH(O$R^6$). In a preferred implementation, X is C(=O). In certain implementations, m is zero. In other implementations, n is zero and p is zero. In certain implementation m is 1, and optionally $R^4$ is halo or acyl. In certain preferred implementations, $R^4$ is substituted aryl-C(O)— or unsubstituted aryl-C(O)—, more preferably $R^4$ is benzoyl. In certain implementations, each of n and p, independently, is zero or one; and each of $R^3$ and $R^5$, independently, is selected from the group consisting of hydroxyl, methyl, methoxy and fluoro.

In certain implementations, the invention provides compounds of formula II:

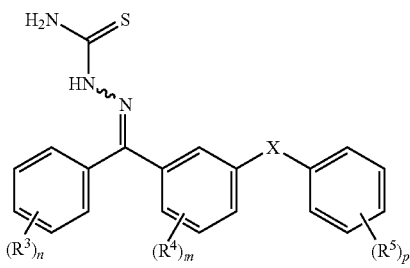

II wherein X, $R^3$, $R^4$, $R^5$, n, m and p are as defined above. Preferably, n, m and p independently are zero or one. In some implementations, both $R^1$ and $R^2$ are hydrogen. In other implementations, n is one and $R^3$ is selected from the group consisting of hydroxyl, methyl, methoxy, and fluoro. In alternative implementations, p is one and $R^5$ is selected from the group consisting of hydroxyl, methyl, methoxy and fluoro. In yet other implementations, $R^4$ is selected from the group consisting of halo and acyl.

In a preferred implementation, the invention provides compounds of formula II-a

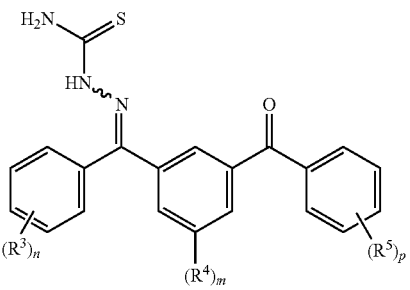

II-a wherein m is zero or one and $R^3$, $R^4$, $R^5$, n, and p are as defined above. Preferably, n and p independently are zero or one. In other implementations, n is one and $R^3$ is selected from the group consisting of hydroxyl, methyl, methoxy, and fluoro. In alternative implementations, p is one and $R^5$ is selected from the group consisting of hydroxyl, methyl, methoxy and fluoro. In a preferred implementation, m is zero. In other implementations, m is one and $R^4$ is selected from the group consisting of halo and acyl.

In yet another implementation, the invention provides compounds of formula II-b

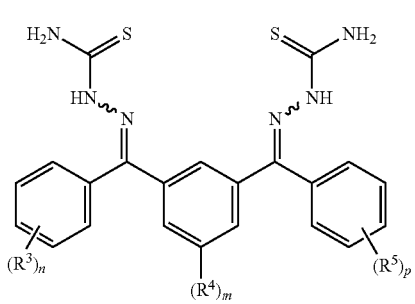

II-b wherein m is zero or one and $R^3$, $R^4$, $R^5$, n, and p are as defined above. Preferably, n and p independently are zero or one. In a preferred implementation, m is zero.

In other implementations, the invention provides compounds of formula III:

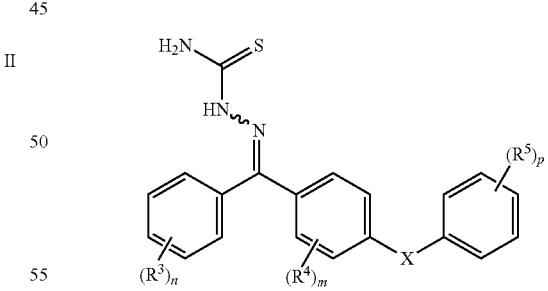

III wherein X, $R^3$, $R^4$, $R^5$, n, m and p are as defined above. Preferably, n, m and p independently are zero or one. In some implementations, both $R^1$ and $R^2$ are hydrogen. In other implementations, n is one and $R^3$ is selected from the group consisting of hydroxyl, methyl, methoxy, and fluoro. In alternative implementations, p is one and $R^5$ is selected from the group consisting of hydroxyl, methyl, methoxy and fluoro. In yet other implementations, $R^4$ is selected from the group consisting of halo and acyl.

In a preferred implementation, the invention provides compounds of formula III-a

11

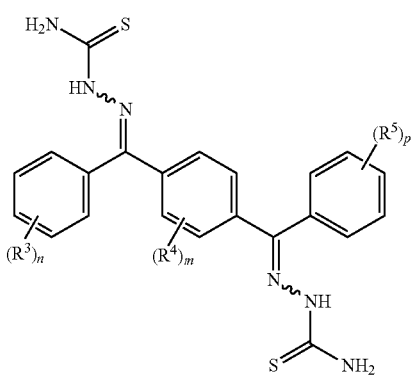

III-a wherein $R^3$, $R^4$, $R^5$, n, m and p are as defined above. Preferably, n, m and p independently are zero or one. In other implementations, n is one and $R^3$ is selected from the group consisting of hydroxyl, methyl, methoxy, and fluoro. In alternative implementations, p is one and $R^5$ is selected from the group consisting of hydroxyl, methyl, methoxy and fluoro. In a preferred implementation, m is zero. In other implementations, m is one and $R^4$ is selected from the group consisting of halo and acyl.

Another aspect of the invention provides a compound selected from Table 1 or Table 2, or a solvate, tautomer, stereoisomer and/or pharmaceutically acceptable salt thereof.

TABLE 1

| Compound | X | $R^1$ | $R^2$ | $(R^3)_n$ | $(R^4)_m$ | $(R^5)_p$ |
|---|---|---|---|---|---|---|
| 3 | —C(=O)— | H | H | n = 0 | m = 0 | p = 0 |
| 6 | —CH(OH)— | H | H | n = 0 | m = 0 | p = 0 |
| 9 | —C(=O)— | H | H | 3-Me | m = 0 | 3-Me |
| 11 | —C(=O)— | H | H | 2-F | 5-Br | 2-F |
| 13 | —C(=O)— | H | H | 4-F | m = 0 | 4-F |
| 15 | —C(=O)— | H | H | 4-OCH₃ | m = 0 | 4-OCH₃ |
| 17 | —C(=O)— | H | H | 4-OH | m = 0 | 4-OCH₃ |
| 18 | —C(=O)— | H | H | 4-OCH₃ | m = 0 | 4-OH |
| 19 | (thiosemicarbazone group) | H | H | 4-OH | m = 0 | 4-OCH₃ |
| 22 | —C(=O)— | H | H | 4-OCH(CH₃)₂ | m = 0 | 4-OCH(CH₃)₂ |
| 23 | (thiosemicarbazone group) | H | H | 4-OCH(CH₃)₂ | m = 0 | 4-OCH(CH₃)₂ |
| 24 | (thiosemicarbazone group) | H | H | 4-Br | m = 0 | 4-Br |
| 25 | —C(=O)— | H | H | n = 0 | 5-benzoyl | p = 0 |
| 26 | —C(=O)— | H | H | 4-Br | m = 0 | 4-Br |
| 27 | —C(=O)— | CH₃ | H | n = 0 | m = 0 | p = 0 |
| 28 | —C(=O)— | H | CH₃ | n = 0 | m = 0 | p = 0 |

TABLE 1-continued

[Structure: thiosemicarbazone with R¹-NH-C(=S)-NH-N(R²)-N=C linking two phenyl rings (R³)ₙ and (R⁴)ₘ, with X linker to third phenyl ring (R⁵)ₚ]

| Compound | X | R¹ | R² | (R³)ₙ | (R⁴)ₘ | (R⁵)ₚ |
|---|---|---|---|---|---|---|
| 32 | [C=N-NH-C(=S)-NH₂ substituent] | H | H | 4-F | m = 0 | 4-F |
| 33 | [C=N-NH-C(=S)-NH₂ substituent] | H | H | 4-OCH₃ | m = 0 | 4-OCH₃ |
| 34 | —C(=O)— | H | H | 4-OH | m = 0 | 4-OH |

TABLE 2

[Structure: H₂N-C(=S)-NH-N=C linking phenyl (R³)ₙ and phenyl (R⁴)ₘ, with X to phenyl (R⁵)ₚ]

| Compound | X | (R³)ₙ | (R⁴)ₘ | (R⁵)ₚ |
|---|---|---|---|---|
| 4 | —C(=O)— | n = 0 | m = 0 | p = 0 |
| 29 | —C(=O)— | 4-F | m = 0 | 4-F |
| 30 | —C(=O)— | 4-Br | m = 0 | 4-Br |
| 31 | —C(=O)— | 4-OCH₃ | m = 0 | 4-OCH₃ |

Depending upon the nature of the various substituents, the thiosemicarbazone compounds of the invention can be in the form of salts. Such salts include salts suitable for pharmaceutical uses ("pharmaceutically-acceptable salts"), salts suitable for veterinary uses, etc. Such salts can be derived from acids or bases, as is well-known in the art.

In one implementation, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4 chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion or an aluminum ion) or coordinates with an organic base (e.g., ethanolamine, diethanolamine, triethanolamine, N-methylglucamine, morpholine, piperidine, dimethylamine, diethylamine, triethylamine, ammonia, etc.).

The thiosemicarbazone compounds and salts thereof may also be in the form of hydrates, solvates and N-oxides, as are well-known in the art.

In another implementation, this invention provides a compound found in Table 1 or Table 2, or stereoisomer, tautomer, solvate, or pharmaceutically acceptable salt thereof.

Cysteine proteases are known to bind to their protein substrates through antiparallel beta sheet structures. The discovery of the improved and potent cysteine protease inhibitors of the invention has resulted from the judicious extension of the thiosemicarbazone functionality into rigid carbon skeletons which mimic the beta sheet conformation of the substrates of these proteases and conform well to their relatively rigid active sites (McGrath, et al. *J. Mol. Biol.* (1995), 247: 251-259; Gillmor, et al., *Protein Science*, (1997), 6: 1603-1611; Choe, et al., *Bioorg. Med. Chem. Lett.* (2005), 13:2141-2156; and Huang et al., *Bioorg. Med. Chem.* (2003), 11: 21-29). Indeed, the compounds of the invention are surprisingly potent inhibitors of cysteine protease inhibition, with IC50 values at the low nanomolar level (e.g., 10 nM or less). Accordingly, the compounds of the invention may be employed in the treatment of parasitic disease states such as malaria, leishmaniasis and trypanosomiasis (e.g., Chagas' disease) as inhibitors of parasitic cysteine proteases, including the cathepsin-L like cysteine proteases (e.g., cruzain). Moreover, the compounds of the invention also find use in the treatment of other mammalian disorders (e.g., cancer and inflammatory disorders) as inhibitors of related mammalian cysteine proteases, including cathepsin L, cathepsin B, cathepsin H, cathepsin K and cathepsin S.

The compounds described herein are potent and selective inhibitors of cathepsin. As a consequence of this activity, the compounds can be used in a variety of in vitro, in vivo and ex vivo contexts to inhibit cathepsin activity.

In one implementation, the method further comprises contacting the cathepsin with the compound in a cell. In another implementation, said contacting occurs in vivo. In another implementation, said contacting occurs in vitro.

In another implementation, the present invention provides a method of treating a disorder mediated by a cathepsin, comprising administering to a patient in need thereof a therapeutically effective amount of a compound effective to treat the disorder wherein the compound is a compound of formula I.

In yet another implementation, the disorder mediated by a cathepsin is a cancer where a cathepsin such as cathepsin K or cathepsin L is upregulated, such as cancers of both epithelial and mesenchymal origin including breast, brain, lung, gastrointestinal, pancreatic, colorectal, melanoma, and head and neck cancers among others. The present compounds also may have a therapeutic effect in tumors such as T cell leukemia, thymoma, T and B cell lymphoma (such as diffuse large B cell lymphoma or transformed (CD20+) indolent lymphoma), colon carcinoma, prostate cancer, ovarian cancer (e.g. ovarian epithelial or primary peritoneal carcinoma) and lung carcinoma (e.g., non-small cell lung cancer or small-cell lung cancer).

Pharmaceutical compositions comprising the thiosemicarbazone compounds described herein can be manufactured by means of conventional mixing, dissolving, granulating, dragee-making, levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

The thiosemicarbazone compound can be formulated in the pharmaceutical compositions per se, or in the form of a hydrate, solvate, N-oxide or pharmaceutically acceptable salt, as described herein. Typically, such salts are more soluble in aqueous solutions than the corresponding free acids and bases, but salts having lower solubility than the corresponding free acids and bases may also be formed.

In one implementation, this invention provides a pharmaceutical formulation comprising a compound selected from the compounds of this invention, as described above.

The compounds can be provided in a variety of formulations and dosages. The compounds can be provided in a pharmaceutically acceptable form including, where the compound can be formulated in the pharmaceutical compositions per se, or in the form of a hydrate, solvate, N-oxide or pharmaceutically acceptable salt, as described herein. Typically, such salts are more soluble in aqueous solutions than the corresponding free acids and bases, but salts having lower solubility than the corresponding free acids and bases may also be formed.

In one implementation, the compounds are provided as non-toxic pharmaceutically acceptable salts, as noted previously. Suitable pharmaceutically acceptable salts of the compounds of this invention include acid addition salts such as those formed with hydrochloric acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The pharmaceutically acceptable salts of the present invention can be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope solvates of the thiosemicarbazone compounds and salts thereof, for example, hydrates.

The thiosemicarbazone compounds may have one or more asymmetric centers, and may accordingly exist both as enantiomers and as diastereomers. It is to be understood that all such isomers and mixtures thereof are encompassed within the scope of the present invention.

The thiosemicarbazone compounds can be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients and vehicles appropriate for each route of administration. In addition to the treatment of warm-blooded animals such as mice, rats, horses, cattle, sheep, dogs, cats, monkeys, etc., the compounds of the invention can be effective in humans.

The pharmaceutical compositions for the administration of the thiosemicarbazone compounds may conveniently be presented in dosage unit form and can be prepared by any of the methods well known in the art of pharmacy. The pharmaceutical compositions can be, for example, prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired therapeutic effect. For example, pharmaceutical compositions of the invention may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) of this invention can be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection can be presented in unit dosage form, e.g., in ampules or in multidose containers, and may contain added preservatives.

Alternatively, the injectable formulation can be provided in powder form for reconstitution with a suitable vehicle, including but not limited to sterile pyrogen free water, buffer, dextrose solution, etc., before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars, films or enteric coatings. Additionally, the pharmaceutical compositions containing the 2,4-substituted pyrmidinediamine as active ingredient in a form suitable for oral use, may also include, for example, troches, lozenges, aqueous or oily suspensions, dispersible powders or granules, emulsions, hard or soft capsules, or syrups or elixirs. Compositions intended for oral use can be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients can be for example, inert diluents, such as calcium carbonate, sodium carbonate, lactose, calcium phosphate or sodium phosphate; granulating and disintegrating agents (e.g., corn starch, or alginic acid); binding agents (e.g. starch, gelatin or acacia); and lubricating agents (e.g. magnesium stearate, stearic acid or talc). The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. They may also be coated by the techniques described in the U.S. Pat. Nos. 4,256,108; 4,166,452; and 4,265,874 to form osmotic therapeutic tablets for control release. The pharmaceutical compositions of the invention may also be in the form of oil-in-water emulsions.

Liquid preparations for oral administration may take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol, Cremophore™ or fractionated vegetable oils); and preservatives (e.g., methyl or propyl p hydroxybenzoates or sorbic acid). The preparations may also contain buffer salts, preservatives, flavoring, coloring and sweetening agents as appropriate.

Preparations for oral administration can be suitably formulated to give controlled release of the active compound, as is well known.

For buccal administration, the compositions may take the form of tablets or lozenges formulated in conventional manner.

For rectal and vaginal routes of administration, the active compound(s) can be formulated as solutions (for retention enemas) suppositories or ointments containing conventional suppository bases such as cocoa butter or other glycerides.

For nasal administration or administration by inhalation or insufflation, the active compound(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

The pharmaceutical compositions can be in the form of a sterile injectable aqueous or oleagenous suspension. This suspension can be formulated according to the known art using those suitable dispersing or wetting agents and suspending agents which have been mentioned above. The sterile injectable preparation may also be a sterile injectable solution or suspension in a non-toxic parenterally-acceptable diluent or solvent. Among the acceptable vehicles and solvents that can be employed are water, Ringer's solution and isotonic sodium chloride solution. The thiosemicarbazone compounds may also be administered in the form of suppositories for rectal or urethral administration of the drug. In particular implementations, the compounds can be formulated as urethral suppositories, for example, for use in the treatment of fertility conditions, particularly in males, e.g., for the treatment of testicular dysfunction.

According to the invention, thiosemicarbazone compounds can be used for manufacturing a composition or medicament, including medicaments suitable for rectal or urethral administration. The invention also relates to methods for manufacturing compositions including thiosemicarbazone compounds in a form that is suitable for urethral or rectal administration, including suppositories.

For topical use, creams, ointments, jellies, gels, solutions or suspensions, etc., containing the thiosemicarbazone compounds can be employed. In certain implementations, the thiosemicarbazone compounds can be formulated for topical administration with polyethylene glycol (PEG). These formulations may optionally comprise additional pharmaceutically acceptable ingredients such as diluents, stabilizers and/or adjuvants. In particular implementations, the topical formulations are formulated for the treatment of allergic conditions and/or skin conditions including psoriasis, contact dermatitis and atopic dermatitis, among others described herein.

According to the invention, thiosemicarbazone compounds can be used for manufacturing a composition or medicament, including medicaments suitable for topical administration. The invention also relates to methods for manufacturing compositions including thiosemicarbazone compounds in a form that is suitable for topical administration.

According to the present invention, thiosemicarbazone compounds can also be delivered by any of a variety of inhalation devices and methods known in the art, including, for example: U.S. Pat. No. 6,241,969; U.S. Pat. No. 6,060,069; U.S. Pat. No. 6,238,647; U.S. Pat. No. 6,335,316; U.S. Pat. No. 5,364,838; U.S. Pat. No. 5,672,581; WO96/32149; WO95/24183; U.S. Pat. No. 5,654,007; U.S. Pat. No. 5,404,871; U.S. Pat. No. 5,672,581; U.S. Pat. No. 5,743,250; U.S. Pat. No. 5,419,315; U.S. Pat. No. 5,558,085; WO98/33480; U.S. Pat. No. 5,364,833; U.S. Pat. No. 5,320,094; U.S. Pat. No. 5,780,014; U.S. Pat. Nos. 5,658,878; 5,518,998; 5,506,203; U.S. Pat. No. 5,661,130; U.S. Pat. No. 5,655,523; U.S. Pat. No. 5,645,051; U.S. Pat. No. 5,622,166; U.S. Pat. No. 5,577,497; U.S. Pat. No. 5,492,112; U.S. Pat. No. 5,327,883; U.S. Pat. No. 5,277,195; U.S. Pat. Pub. No. 20010041190; U.S. Pat. Pub. No. 20020006901; and U.S. Pat. Pub. No. 20020034477.

Included among the devices which can be used to administer particular examples of the thiosemicarbazone compounds are those well-known in the art, such as, metered dose inhalers, liquid nebulizers, dry powder inhalers, sprayers, thermal vaporizers, and the like. Other suitable technology for administration of particular thiosemicarbazone compounds includes electrohydrodynamic aerosolizers.

In addition, the inhalation device is preferably practical, in the sense of being easy to use, small enough to carry conveniently, capable of providing multiple doses, and durable. Some specific examples of commercially available inhalation devices are Turbohaler (Astra, Wilmington, Del.), Rotahaler (Glaxo, Research Triangle Park, N.C.), Diskus (Glaxo, Research Triangle Park, N.C.), the Ultravent nebulizer (Mallinckrodt), the Acorn II nebulizer (Marquest Medical Products, Totowa, N.J.) the Ventolin metered dose inhaler (Glaxo, Research Triangle Park, N.C.), or the like. In one implementation, thiosemicarbazone compounds can be delivered by a dry powder inhaler or a sprayer.

As those skilled in the art will recognize, the formulation of thiosemicarbazone compounds, the quantity of the formulation delivered, and the duration of administration of a single dose depend on the type of inhalation device employed as well as other factors. For some aerosol delivery systems, such as nebulizers, the frequency of administration and length of time for which the system is activated will depend mainly on the concentration of thiosemicarbazone compounds in the aerosol. For example, shorter periods of administration can be used at higher concentrations of thiosemicarbazone compounds in the nebulizer solution. Devices such as metered dose inhalers can produce higher aerosol concentrations, and can be operated for shorter periods to deliver the desired amount of thiosemicarbazone compounds in some implementations. Devices such as dry powder inhalers deliver active agent until a given charge of agent is expelled from the device. In this type of inhaler, the amount of 2 thiosemicarbazone compounds in a given quantity of the powder determines the dose delivered in a single administration. The formulation of thiosemicarbazone is selected to yield the desired particle size in the chosen inhalation device.

Formulations of thiosemicarbazone compounds for administration from a dry powder inhaler may typically include a finely divided dry powder containing thiosemicarbazone compounds, but the powder can also include a bulking agent, buffer, carrier, excipient, another additive, or the like. Additives can be included in a dry powder formulation of thiosemicarbazone compounds, for example, to dilute the powder as required for delivery from the particular powder inhaler, to facilitate processing of the formulation, to provide advantageous powder properties to the formulation, to facilitate dispersion of the powder from the inhalation device, to stabilize to the formulation (e.g., antioxidants or buffers), to provide taste to the formulation, or the like. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; or the like.

The present invention also relates to a pharmaceutical composition including thiosemicarbazone compounds suitable for administration by inhalation. According to the invention, thiosemicarbazone compounds can be used for manufacturing a composition or medicament, including medicaments suitable for administration by inhalation. The invention also relates to methods for manufacturing compositions including thiosemicarbazone compounds in a form that is suitable for administration, including administration by inhalation. For example, a dry powder formulation can be manufactured in several ways, using conventional techniques, such as described in any of the publications mentioned above and incorporated expressly herein by reference, and for example, Baker, et al., U.S. Pat. No. 5,700,904, the entire disclosure of which is incorporated expressly herein by reference. Particles in the size range appropriate for maximal deposition in the lower respiratory tract can be made by micronizing, milling, or the like. And a liquid formulation can be manufactured by dissolving the thiosemicarbazone compounds in a suitable solvent, such as water, at an appropriate pH, including buffers or other excipients.

Pharmaceutical compositions comprising the thiosemicarbazone compounds described herein can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

For ocular administration, the thiosemicarbazone compound(s) can be formulated as a solution, emulsion, suspension, etc. suitable for administration to the eye. A variety of vehicles suitable for administering compounds to the eye are known in the art. Specific non-limiting examples are described in U.S. Pat. No. 6,261,547; U.S. Pat. No. 6,197,934; U.S. Pat. No. 6,056,950; U.S. Pat. No. 5,800,807; U.S. Pat. No. 5,776,445; U.S. Pat. No. 5,698,219; U.S. Pat. No. 5,521,222; U.S. Pat. No. 5,403,841; U.S. Pat. No. 5,077,033; U.S. Pat. No. 4,882,150; and U.S. Pat. No. 4,738,851.

For prolonged delivery, the thiosemicarbazone compound(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008, 110; and U.S. Pat. No. 4,921,475.

Alternatively, other pharmaceutical delivery systems can be employed. Liposomes and emulsions are well-known examples of delivery vehicles that can be used to deliver active compound(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device can be accompanied by instructions for administration.

The amount of compound administered will depend upon a variety of factors, including, for example, the particular condition being treated, the mode of administration, the severity of the condition being treated and the age and weight of the patient, the bioavailability of the particular active compound, etc. Determination of an effective dosage is well within the capabilities of those skilled in the art.

As known by those of skill in the art, the preferred dosage of thiosemicarbazone compounds will also depend on the age, weight, general health and severity of the condition of the individual being treated. Dosage may also need to be tailored to the sex of the individual and/or where administered by inhalation, the lung capacity of the individual. Dosage may also be tailored to individuals suffering from more than one condition or those individuals who have additional conditions which affect lung capacity and the ability to breathe normally, for example, emphysema, bronchitis, pneumonia, respiratory infections, etc. Dosage, and frequency of administration of the compounds will also depend on whether the compounds are formulated for treatment of acute episodes of a condition or for the prophylactic treatment of a disorder. For example, acute episodes of allergic conditions, including allergy-related asthma, transplant rejection, etc. A skilled practitioner will be able to determine the optimal dose for a particular individual.

For prophylactic administration, the compound can be administered to a patient at risk of developing one of the previously described conditions. For example, if it is unknown whether a patient is allergic to a particular drug, the compound can be administered prior to administration of the drug to avoid or ameliorate an allergic response to the drug. Alternatively, prophylactic administration can be applied to avoid the onset of symptoms in a patient diagnosed with the underlying disorder. For example, a compound can be administered to an allergy sufferer prior to expected exposure to the allergen. Compounds may also be administered prophylactically to healthy individuals who are repeatedly exposed to agents known to one of the above-described maladies to prevent the onset of the disorder. For example, a compound can be administered to a healthy individual who is repeatedly exposed to an allergen known to induce allergies, such as latex, in an effort to prevent the individual from developing an allergy. Alternatively, a compound can be administered to a patient suffering from asthma prior to partaking in activities which trigger asthma attacks to lessen the severity of, or avoid altogether, an asthmatic episode.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, etc. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an $IC_{50}$ of the particular compound as measured in as in vitro assay. Calculating dosages to achieve such circulating blood or serum concentrations taking into account the bioavailability of the particular compound is well within the capabilities of skilled artisans. For guidance, the reader is referred to Fingl & Woodbury, "*General Principles,*" In: Goodman and Gilman's *The Pharmaceutical Basis of Therapeutics*, Chapter 1, pp. 1-46, latest edition, Pergamagon Press, and the references cited therein.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, (1995) *Allergy* 50(21 Suppl):6-9, discussion 34-38 and Tumas et al., (2001), *J. Allergy Clin. Immunol.* 107(6): 1025-1033. Suitable animal models of allergic rhinitis are described in Szelenyi et al., (2000), *Arzneimittelforschung* 50(11):1037-42; Kawaguchi et al., (1994), *Clin. Exp. Allergy* 24(3):238-244 and Sugimoto et al., (2000), *Immunopharmacology* 48(1):1-7. Suitable animal models of allergic conjunctivitis are described in Carreras et al., (1993), *Br. J. Ophthalmol.* 77(8):509-514; Saiga et al., (1992), *Ophthalmic Res.* 24(1):45-50; and Kunert et al., (2001), *Invest. Ophthalmol. Vis. Sci.* 42(11):2483-2489. Suitable animal models of systemic mastocytosis are described in O'Keefe et al., (1987), *J. Vet. Intern. Med.* 1(2):75-80 and Bean-Knudsen et al., (1989), *Vet. Pathol.* 26(1):90-92. Suitable animal models of hyper IgE syndrome are described in Claman et al., (1990), *Clin. Immunol. Immunopathol.* 56(1):46-53. Suitable animal models of B-cell lymphoma are described in Hough et al., (1998), *Proc. Natl. Acad. Sci. USA* 95:13853-13858 and Hakim et al., (1996), *J. Immunol.* 157(12):5503-5511. Suitable animal models of atopic disorders such as atopic dermatitis, atopic eczema and atopic asthma are described in Chan et al., (2001), *J. Invest. Dermatol.* 117(4):977-983 and Suto et al., (1999), *Int. Arch. Allergy Immunol.* 120(Suppl 1):70-75. Suitable animal models of transplant rejection, such as models of HVGR are described in O'Shea et al., (2004), *Nature Reviews Drug Discovery* 3:555-564; Cetkovic-Curlje & Tibbles, (2004), *Current Pharmaceutical Design* 10:1767-1784; and Chengelian et al., (2003), *Science* 302:875-878. Ordinarily skilled artisans can routinely adapt such information to determine dosages suitable for human administration.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration and various factors discussed above. Dosage amount and interval can be adjusted individually to provide plasma levels of the compound(s) which are sufficient to maintain therapeutic or prophylactic effect. For example, the compounds can be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

Also provided are kits for administration of the thiosemicarbazone or pharmaceutical formulations comprising the compound, that may include a dosage amount of at least one thiosemicarbazone or a composition comprising at least one thiosemicarbazone as disclosed herein. Kits may further comprise suitable packaging and/or instructions for use of the compound. Kits may also comprise a means for the delivery of the at least one thiosemicarbazone or compositions comprising at least thiosemicarbazone, such as an inhaler, spray dispenser (e.g. nasal spray), syringe for injection or pressure pack for capsules, tables, suppositories, or other device as described herein.

Additionally, the compounds of the present invention can be assembled in the form of kits. The kit provides the compound and reagents to prepare a composition for administration. The composition can be in a dry or lyophilized form, or in a solution, particularly a sterile solution. When the composition is in a dry form, the reagent may comprise a pharmaceutically acceptable diluent for preparing a liquid formulation. The kit may contain a device for administration or for dispensing the compositions, including, but not limited to syringe, pipette, transdermal patch, or inhalant.

The kits may include other therapeutic compounds for use in conjunction with the compounds described herein. In one implementation, the therapeutic agents are immunosuppressant or anti-allergan compounds. These compounds can be provided in a separate form, or mixed with the compounds of the present invention.

The kits will include appropriate instructions for preparation and administration of the composition, side effects of the compositions, and any other relevant information. The instructions can be in any suitable format, including, but not limited to, printed matter, videotape, computer readable disk, or optical disc.

In one implementation, this invention provides a kit comprising a compound selected from the compounds of this invention, packaging, and instructions for use.

Kits may also be provided that contain sufficient dosages of thiosemicarbazone or composition to provide effective treatment for an individual for an extended period, such as a week, 2 weeks, 3, weeks, 4 weeks, 6 weeks or 8 weeks or more.

It will be appreciated by one of skill in the art that the implementations summarized above may be used together in any suitable combination to generate additional implementations not expressly recited above, and that such implementations are considered to be part of the present invention.

V. EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims. The following abbreviations were used as noted (Table 3):

TABLE 3

Table of Abbreviations

| | |
|---|---|
| BRIJ ® 35 | Polyethylene glycol dodecyl ether Polyoxyethylene (23) lauryl ether $C_{12}H_{25}(OCH_2CH_2)_nOH$, n~23 |
| DMSO | dimethylsulfoxide |
| DTT | dithiothreitol |
| EDTA | ethylenediaminetetraacetic acid |
| h | hour(s) |
| HPLC | High-Performance Liquid Chromatography |
| HRMS (ESI) | High Resolution Mass Spectrometry (Electrospray Ionization) |
| $IC_{50}$ | half maximal inhibitory concentration |
| LC-MS | liquid chromatography- mass spectrometry |
| MeOH | methanol |
| TsOH | p-toluenesulfonic acid |

A. 1,4-dibenzoylbenzene (1)

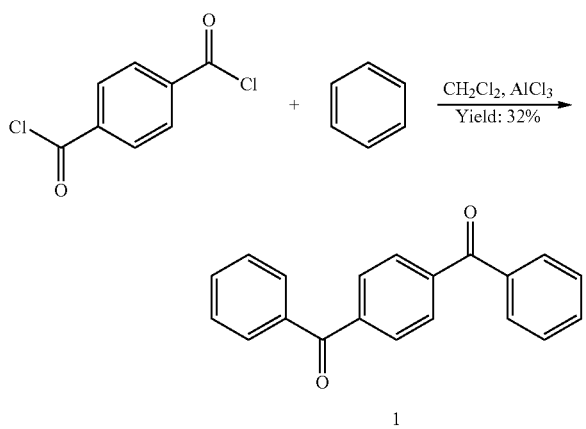

Aluminum trichloride (1.37 g, 10.33 mmol) was added to a solution of terephthaloyl dichloride (1.0 g, 4.42 mmol) in anhydrous dichloromethane and excess benzene. After stirring for 12 h at room temperature under an inert atmosphere of nitrogen gas, the reaction mixture treated with 10% HCl (50 mL) and the products were extracted with ethyl acetate (3×20 mL). The combined organic phases were washed with brine and dried over sodium sulfate. After the organic layer was concentrated under reduced pressure, purification using flash chromatography (silica gel, hexanes:ethyl acetate, 80:20) afforded 1,4-dibenzoyl benzene 1 (0.405 g, 1.41 mmol) in a 32% yield.

B. 3-benzoyl benzophenone thiosemicarbazone (3), 2-[(3-benzoylphenyl)(phenyl)methylene]-N-methyl-hydrazinecarbothioamide (27), and 2-[(3-benzoylphenyl)(phenyl)methylene]-1-methylhydrazinecarbothioamide (28)

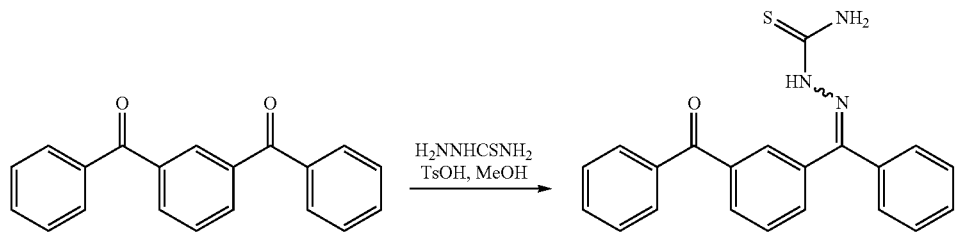

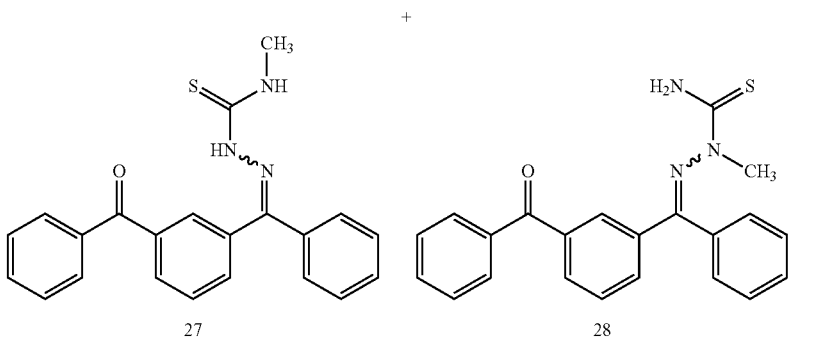

p-toluenesulfonic acid (0.026 g, 0.02 mmol) was added to a solution of 1,3 dibenzoylbenzene 2 (2.00 g, 6.98 mmol) in anhydrous methanol (20 mL). After stirring at reflux for 10 min, thiosemicarbazide (0.476 g, 5.235 mmol) was added to the reaction mixture and stirred for 26 h under an inert atmosphere of nitrogen gas. After 26 h, methanol was removed under reduced pressure and 50 mL of water was then added. The products were extracted with ethyl acetate (2×50 mL) and the combined organic phases were washed with brine, dried over anhydrous sodium sulfate, and the solvent was removed under reduced pressure. Purification using flash chromatography (silica gel, hexanes:ethyl acetate, gradient 90:10 to 52:48) afforded 3-benzoyl benzophenone thiosemicarbazone 3 (0.829 g, 5.235 mmol) as a light yellow solid in a 44% yield. HRMS (ESI) calculated for $C_{21}H_{17}N_3OSH^+$ $(M+H)^+$ 360.11651, found 360.11654. The isolated product 3 was 99.3% pure by HPLC at 300 and 320 nm; retention time 7.225 (method: 0-25 min, 50 to 100% acetonitrile, 50 to 0% water). This purified product was submitted for biological testing.

Compounds 27 and 28 are a byproduct obtained in the synthesis of Compound 3. HRMS (ESI) calculated for $C_{22}H_{20}ON_3SH_+$ (M+H) 374.1322, found 374.1324. The isolated yield of compounds 27 and 28 were 2.5% and 2.4%, respectively. The location of the attachment of the methyl group has not been confirmed.

C. 4-Benzoyl benzophenone thiosemicarbazone (4)

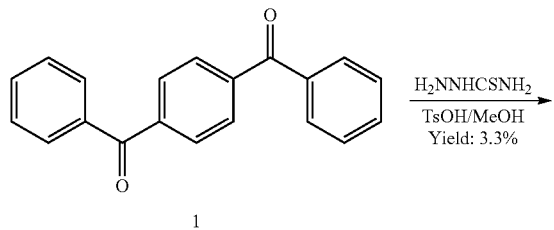

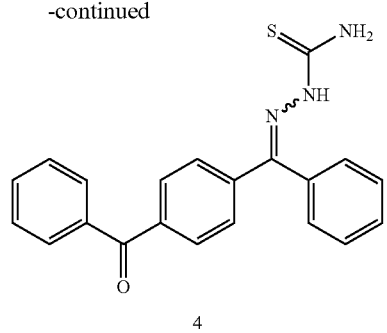

A catalytic amount of p-toluenesulfonic acid was added to a solution of 1,4 dibenzoylbenzene 1 (0.286 g, 1 mmol) in anhydrous methanol (10 mL). After stirring at reflux for 10 min, thiosemicarbazide (0.182 g, 2 mmol) was added to the reaction mixture and stirred for 12 h under an inert atmosphere of nitrogen gas. After 12 h, methanol was removed under reduced pressure and 10 mL of water was then added. The products were extracted with ethyl acetate (2×20 mL) and the combined organic phases were washed with brine, dried over anhydrous sodium sulfate, and the solvent was removed under reduced pressure. Purification using flash chromatography (silica gel, hexanes:ethyl acetate, gradient 70:30) afforded 4-benzoyl benzophenone thiosemicarbazone 4 (0.012 g, 0.033 mmol) in a 3.3% yield. HRMS (ESI) calculated for $C_{21}H_{17}N_3OSH^+$ $(M+H)^+$ 360.11651, found 360.11649.

D. 3-Benzoyl benzhydrol thiosemicarbazone (6)

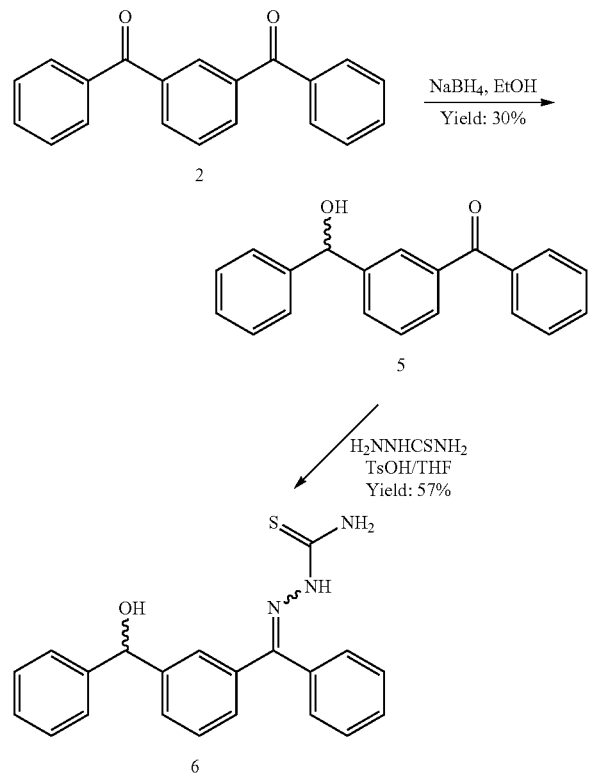

1,3 dibenzoylbenzene 2 (2.00 g, 6.98 mmol) was dissolved in anhydrous ethanol (20 mL) under an inert atmosphere of nitrogen gas. The reaction mixture was cooled to 0° C. followed by the addition of sodium borohydride (0.090 g, 2.094 mmol). The reaction mixture was stirred for 4 h and quenched the addition of a small amount of water. The reaction mixture was concentrated under reduced pressure and the products were extracted from water with ethyl acetate (2×50 mL). The combined organic phases were washed with brine, dried over anhydrous sodium sulfate, and the solvent was removed under reduced pressure. Purification using flash chromatography (silica gel, hexanes:ethyl acetate, gradient 93:7 to 30:70) afforded 3-benzoyl benzhydrol 5 (0.601 g, 2.084 mmol) in a 30% yield.

p-toluenesulfonic acid (0.007 g, 0.03 mmol) was added to a solution of 3-benzoyl benzhydrol 5 (0.396 g, 1.09 mmol) in anhydrous tetrahydrofuran (10 mL). After stirring at reflux for 10 min, thiosemicarbazide (0.199 g, 2.19 mmol) was added to the reaction mixture and stirred for 2 days under an inert atmosphere of nitrogen gas. After 2 days, tetrahydrofuran was removed under reduced pressure and water (50 mL) was added. The products were extracted with ethyl acetate (2×20 mL) and the combined organic phases were washed with brine, dried over anhydrous sodium sulfate, and the solvent was removed under reduced pressure. Purification using flash chromatography (silica gel, hexanes:ethyl acetate, gradient 88:12 to 0:100) afforded 3-benzoyl benzhydrol thiosemicarbazone 6 (0.228 g, 0.631 mmol) as a white solid in a 57% yield. HRMS (ESI) calculated for $C_{21}H_{19}N_3OSH^+$ $(M+H)^+$ 362.1321, found 362.1336.

E. 1-(3-methylbenzoyl),3-(3-methylbenzoyl)benzene thisosemicarbazone (9)

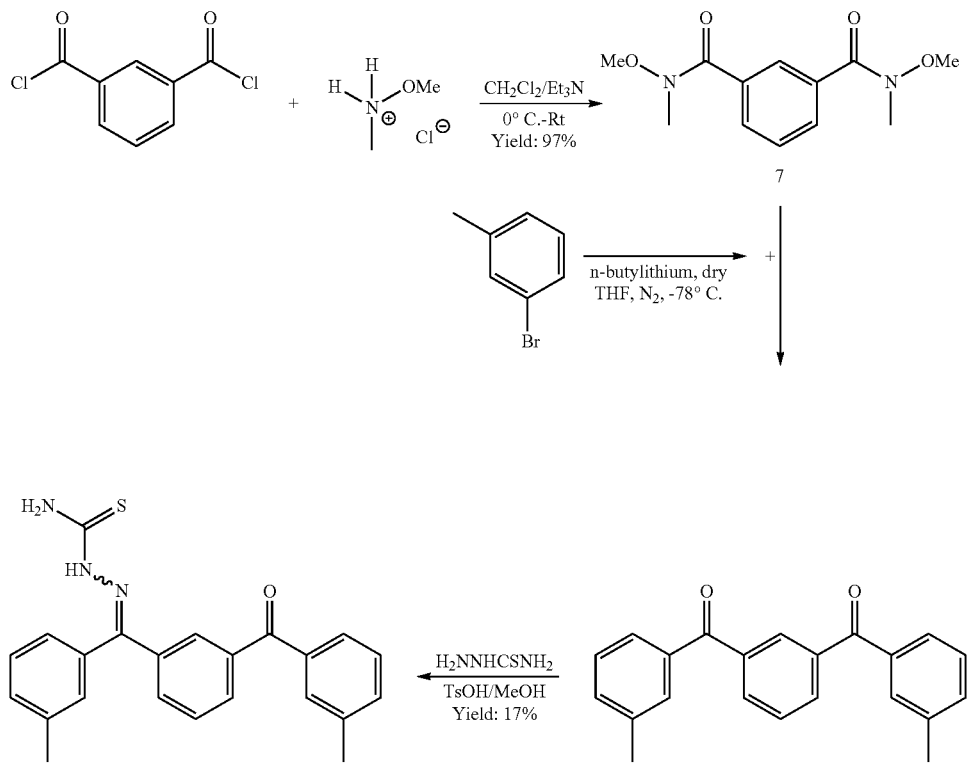

Triethylamine (5.61 mL, 40 mmol) was added dropwise to a solution of N,O-dimethylhydroxylamine hydrochloride (2.926 g, 30 mmol) in anhydrous dichloromethane (35 mL) at 0° C. After stirring for 10 min, isophthaloyl dichloride (2.03 g, 10 mmol) dissolved in 6 mL of anhydrous dichloromethane was added dropwise. The reaction mixture was returned to room temperature and stirred for 5 h. The reaction mixture was quenched with water (50 mL) and the products were extracted with dichloromethane (2×50 mL). The combined organic phases were washed with brine, dried over anhydrous sodium sulfate, and the solvent was removed under reduced pressure. Purification using flash chromatography (silica gel, dichloromethane:methanol, 95:5) afforded $N^1,N^3$-bis-methoxy-1,3-benzenedicarboxamide 7 (2.465 g, 9.77 mmol) in a 97% yield.

dichloromethane (2×30 mL) and the combined organic phases were washed with brine, dried over anhydrous sodium sulfate, and the solvent was removed under reduced pressure. Purification using flash chromatography (silica gel, hexanes: ethyl acetate, gradient 90:10 to 80:20) afforded 1-(3-methylbenzoyl),3-(3-methylbenzoyl)benzene thiosemicarbazone 9 (0.063 g, 0.016 mmol) as a white solid in a 17% yield. HRMS (ESI) calculated for $C_{23}H_{21}N_3OSH^+$ $(M+H)^+$ 388.14781, found 388.14793. The product was determined to be approximately 80% pure and was submitted for biological testing without further purification.

F. 1,3-bis(2-fluoro-benzoyl)-5-bromobenzene thiosemicarbazone (11)

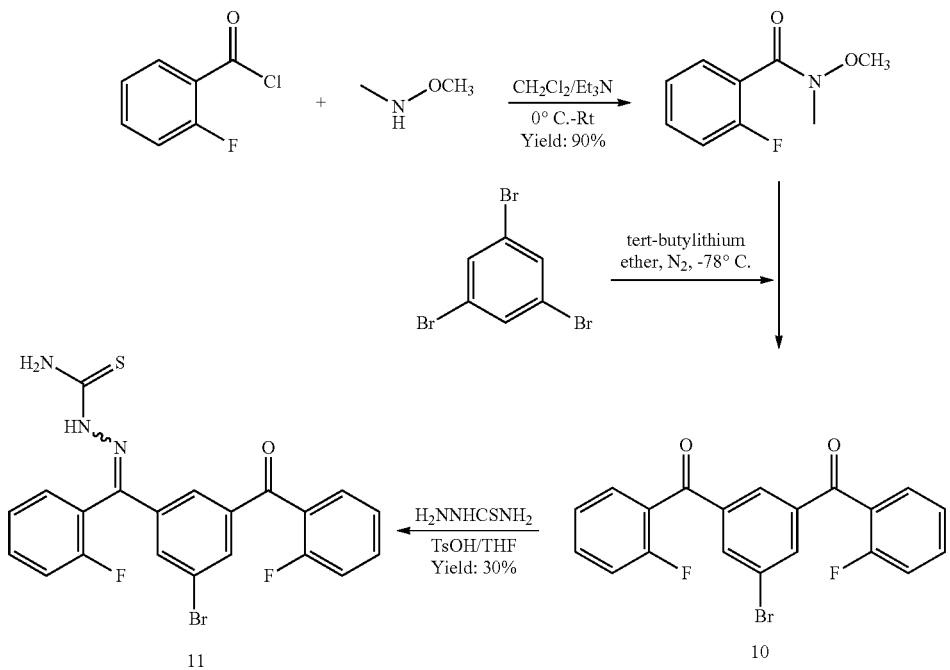

3-bromotoluene (6.684 g, 39.08 mmol) was dissolved in anhydrous tetrahydrofuran (30 mL) under an inert atmosphere of nitrogen. The solution was stirred for 5 min and cooled to −78° C. followed by the dropwise addition of n-butyllithium in hexanes (2.5M; 13.6 mL). After stirring for 3.5 h, the Weinreb amide of isophthaloyl dichloride was added dropwise and the solution was stirred for 1 h at −78° C. The reaction mixture was quenched with 1 M HCl (40 mL) and the products were extracted with dichloromethane (2×50 mL). The combined organic phases were washed with brine, dried over anhydrous sodium sulfate, and the solvent was removed under reduced pressure. Purification using flash chromatography (silica gel, hexanes:ethyl acetate, gradient, 95:5 to 70:30) afforded 2.465 g, 9.77 mmol) 1-(3-methylbenzoyl),3-(3-methylbenzoyl)benzene 8 in a 72% yield.

p-toluenesulfonic acid (0.018 g, 0.09 mmol) was added to a solution of 1-(3-methylbenzoyl),3-(3-methylbenzoyl)benzene 8 (0.300 g, 0.95 mmol) in anhydrous methanol (10 mL). After stirring at reflux for 10 min, thiosemicarbazide (0.086 g, 0.954 mmol) was added to the reaction mixture and stirred for 12 h under an inert atmosphere of nitrogen. After 12 h, methanol was removed under reduced pressure and 10 mL of water was then added. The products were extracted with Triethylamine (5.32 mL, 37.84 mmol) was added dropwise to a solution of N,O-dimethylhydroxylamine hydrochloride (2.768 g, 28.38 mmol) in anhydrous dichloromethane (45 mL) at 0° C. After stirring for 10 min, 2-fluorobenzoyl chloride (0.303 mL, 2.52 mmol) in anhydrous dichloromethane (15 mL) was added dropwise. The reaction mixture was returned to room temperature and stirred for 5 h. The reaction mixture was quenched with water (60 mL) and the products were extracted with dichloromethane (2×60 mL). The combined organic phases were washed with brine, dried over anhydrous sodium sulfate, and the solvent was removed under reduced pressure. Purification using flash chromatography (silica gel, hexanes:ethyl acetate, gradient 93:7 to 60:40) afforded 2-Fluoro-N-methoxy-N-methyl-benzamide (3.116, 17 mmol) in a 90% yield.

Tert-butyllithium in pentane (1.6M, 7.72 mL) was added dropwise to a solution of 1,3,5 tribromobenzene (0.972 g, 3.09 mmol) in anhydrous ether (30 mL) at −78° C. under a flow of nitrogen gas. After 2 h, 2-Fluoro-N-methoxy-N-methyl-benzamide (1.132 g, 6.18 mmol) dissolved in anhydrous ether (5 mL) was added dropwise and the reaction mixture was allowed to slowly come to room temperature and stirred for 24 h. After 24 h, the reaction mixture was quenched with water (30 mL) and the products were extracted with ether (2×50 mL). The combined organic phases were washed with brine, dried over anhydrous sodium sulfate, and the solvent was removed under reduced pressure. Purification using flash chromatography (silica gel, hexanes:ethyl acetate, gradient 95:5 to 60:40) afforded 2-1,3-bis(2-fluoro-benzoyl)-5-bromobenzene 10 (0.617 g, 6.18 mmol) in a 50% yield.

p-toluenesulfonic acid (0.006 g, 0.03 mmol) was added to a solution of 1,3-bis(3-fluoro-benzoyl)-5-bromobenzene 10 (0.190 g, 0.473 mmol) in anhydrous tetrahydrofuran (15 mL). After stirring at reflux for 10 min, thiosemicarbazide (0.088 g, 0.97 mmol) was added to the reaction mixture and stirred for 28 h under an inert atmosphere of nitrogen gas. After 28 h, tetrahydrofuran was removed under reduced pressure and 10 mL of water was then added. The products were extracted with EtOAc (2×50 mL) and the combined organic phases were washed with brine, dried over anhydrous sodium sulfate, and the solvent was removed under reduced pressure. Purification using flash chromatography (silica gel, hexanes:ethyl acetate, gradient 90:11 to 30:70) afforded 1,3-bis(2-fluoro-benzoyl)-5-bromobenzene thiosemicarbazone 11 (0.068 g, 0.143 mmol) in a 30% yield. HRMS (ESI) calculated for $C_{21}H_{14}BrF_2N_3OSH^+$ $(M+H)^+$ 474.0082, found 474.0087.

G. 1,3-bis-(4-fluorobenzoyl)benzene thiosemicarbazone (13)

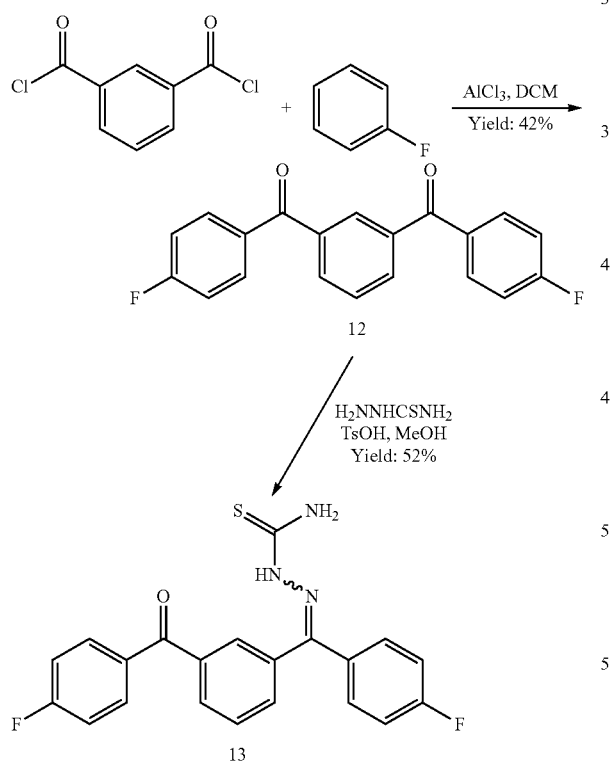

Aluminum trichloride (6.53 g, 49.5 mmol) was added to a solution of isophthaloyl dichloride (5.0 g, 24.8 mmol) in dichloromethane (100 mL). After heating at reflux for 30 min, the monofluorobenzene (2.835 g, 29.5 mmol) was added and stirring was continued at reflux. After stirring over 12 h, the reaction mixture was poured onto the crushed ice. The resulting solution was neutralized with 10% NaOH (100 mL), and extracted with dichloromethane (3×100 mL). The combined organic layer was washed with water, followed by brine and dried over $Na_2SO_4$. After the organic layer was concentrated under reduced pressure, purification using flash chromatography (silica gel, hexanes:ethyl acetate, 60:40) afforded 1,3-bis-(4-fluorobenzoyl)benzene 12 (3.37 g, 10.5 mmol) as a white solid in a 42% yield; 1H NMR (500 MHz, CDCl3): δ 8.130 (t, J=1.5 Hz, 1H, ArH), 8.00 (dd, J=7.5 Hz, 1.5 Hz, 1H, ArH), 7.87 (m, 4H, ArH), 7.64 (t, J=8.0 Hz, 1H, ArH), 7.18 (m, 4H, ArH).

1,3-bis-(4-fluorobenzoyl)benzene 12 (0.347 g, 1.08 mmol) was dissolved in anhydrous methanol (50 mL). The solution was heated at reflux for 15 min, and thiosemicarbazide (0.049 g, 0.54 mmol) and a catalytic amount of p-toluenesulfonic acid were added. After 10 h at reflux, the resulting solution was concentrated under reduced pressure. Purification using flash chromatography (silica gel, hexanes:ethyl acetate, 70:30) afforded the desired 1,3-bis-(4-fluorobenzoyl)benzene thiosemicarbazone (0.11 g, 0.278 mmol, 52% yield) as a white solid; $^1$H NMR (500 MHz, CDCl$_3$): δ 8.67 (s, 1H, NH), 7.97 (m, 1H, ArH), 7.90 (m, 1H, ArH), 7.83 (m, 1H, ArH), 7.75 (m, 1H, ArH), 7.68 (m, 1H, ArH), 7.500 (m, 2H, ArH), 7.39 (s, 1H, NH$_2$), 7.31 (m, 2H, ArH), 7.22 (ddd, J=8.5 Hz, 5.0 Hz, 3.0 Hz, 1H, ArH), 7.16 (ddd, J=8.5 Hz, 5.0 Hz, 3.0 Hz, 1H, ArH), 7.06 (ddd, J=8.5 Hz, 5.0 Hz, 3.0 Hz, 1H, ArH), 6.36 (s, 1H, NH$_2$); HRMS (ESI) calculated for $C_{21}H_{15}F_2N_3OSH$ $(M+H)^+$ 396.0970, found 394.0834; HPLC retention time 13.740, 13.966 min.

H. 1,3-bis-(4-methoxybenzoyl)benzene dithiosemicarbazone (33)

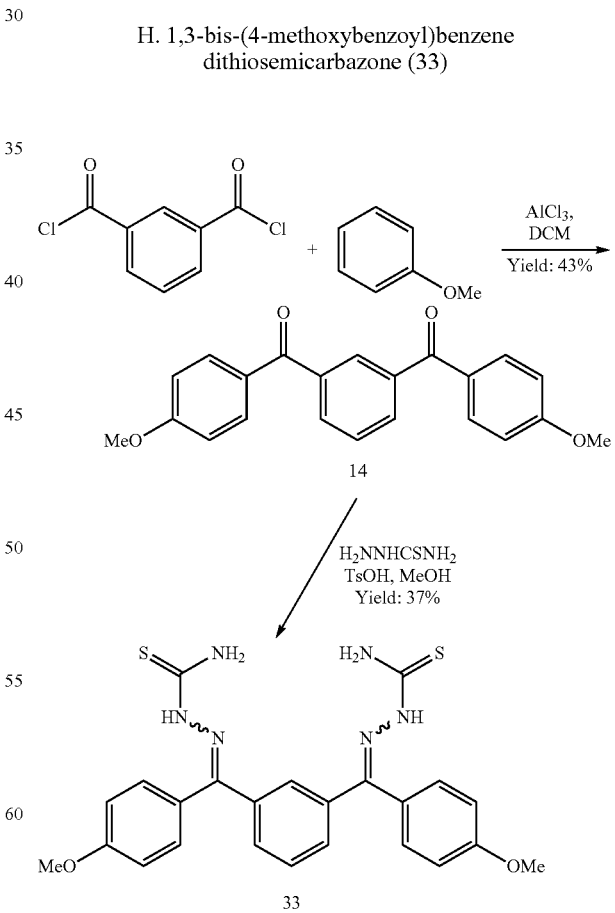

Aluminum trichloride (2.79 g, 21 mmol) was added to a solution of isophthaloyl dichloride (2.0 g, 10 mmol) in dichloromethane (50 mL). After heating at reflux for 30 min, the anisole (1.29 mL, 11.8 mmol) was added and stirring was continued at reflux. After stirring over 20 h, the reaction mixture was poured onto the crushed ice. The resulting solution was neutralized with 10% NaOH (100 mL), and extracted with dichloromethane (3×100 mL). The combined organic layer was washed with water, followed by brine, and dried over $Na_2SO_4$. After the organic layer was concentrated under reduced pressure, the purification using flash chromatography (silica gel, hexanes:ethyl acetate, 60:40) afforded 1,3-bis-(4-methoxy benzoyl)benzene 14 (1.5 g, 4.33 mmol) as a white solid in a 43% yield; $^1$H NMR (500 MHz, $CDCl_3$): δ 8.09 (t, J=1.0 Hz, 1H, ArH), 7.95 (dd, J=7.5 Hz, 1.5 Hz, 2H, ArH), 7.84 (ddd, J=8.9, 4.7, 2.5 Hz, 4H, ArH), 7.61 (td, J=7.5 Hz, 0.4 Hz, 1H, ArH), 6.97 (ddd, J=8.9, 4.9, 2.85 Hz, 4H, ArH), 3.88 (s, 6H, $OCH_3$); $^{13}$C NMR (125 MHz, $CDCl_3$): δ 194.70, 163.53, 138.80, 132.73, 132.60, 1320.61, 129.63, 128.32, 113.76, 55.53.

1,3-bis-(4-methoxybenzoyl)benzene 14 (0.45 g, 1.3 mmol) was dissolved in anhydrous methanol (48 mL). The solution was heated at reflux for 15 min, and thiosemicarbazide (0.059 g, 0.64 mmol) and a catalytic amount of p-toluenesulfonic acid were added. After 10 h at reflux, the mixture was concentrated under reduced pressure. The resulting solid was purified using flash chromatography (hexanes:ethyl acetate, 60:40) to afford the pure 1,3-bis-(4-methoxybenzoyl) benzene dithiosemicarbazone 33 (0.10 g, 0.238 mmol, 37% yield) as a white solid. HRMS (ESI) calculated for $C_{24}H_{25}N_6O_2S_2$ $(M+H)^+$ 493.1475, found 493.1470; HPLC retention time 11.424, 11.664, 11.832 min.

I. 1-(4-hydroxybenzoyl)-3-(4-methoxybenzoyl)benzene thiosemicarbazone (17); 1-(4-methoxybenzoyl)-3-(4-hydroxybenzoyl)benzene thiosemicarbazone (18) and 1-(4-hydroxybenzoyl)-3-(4-methoxybenzoyl)benzene di-thiosemicarbazone (19)

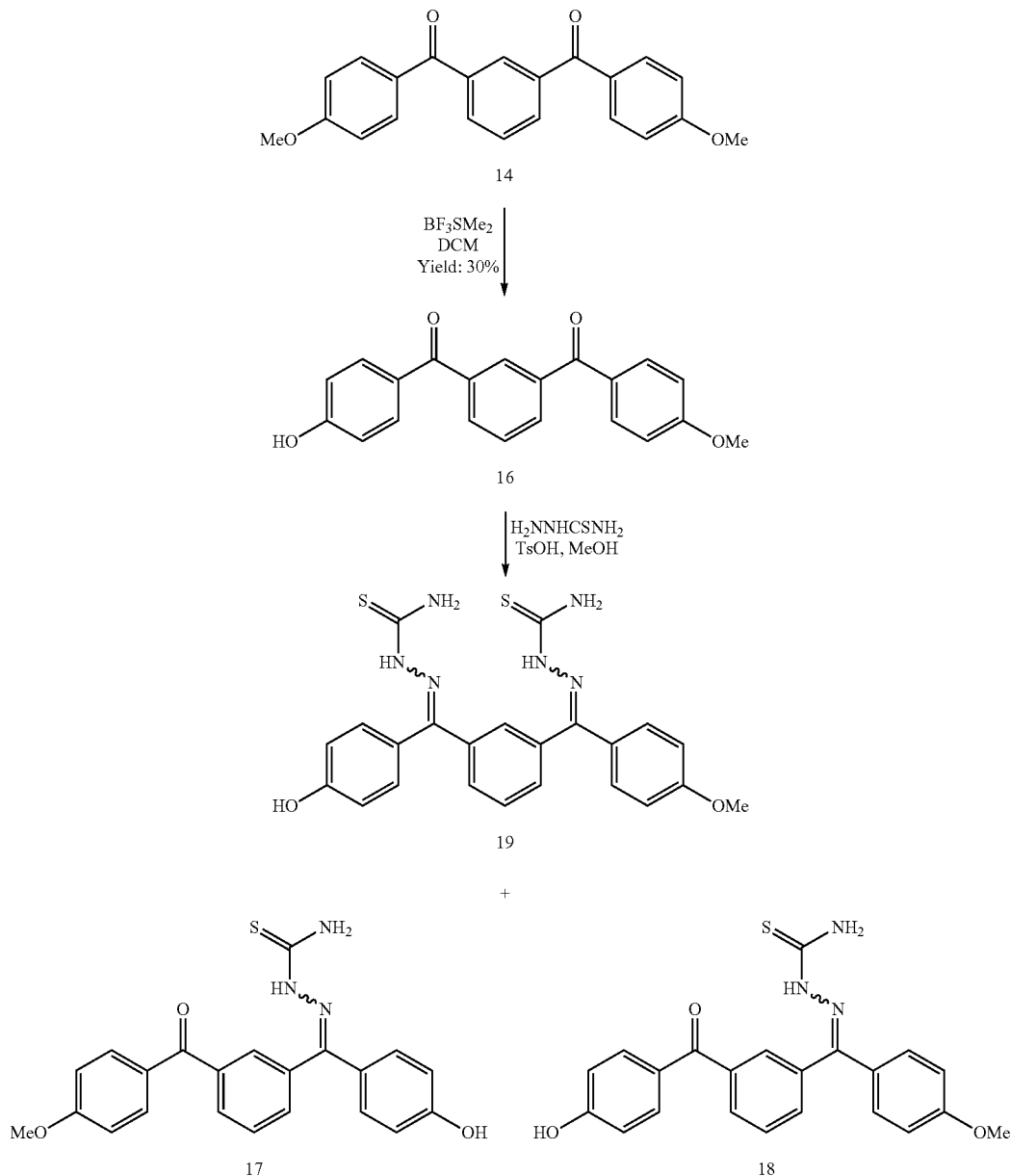

To a well-stirred solution of 1,3-bis-(4-methoxybenzoyl)benzene 14 (700 mg, 2.02 mmol) in dichloromethane (25 mL) was added boron trifluoride dimethyl sulfide complex (BF$_3$.SMe$_2$, 10 mL). The reaction was stirred for 16 h at room temperature, and then quenched with water, and extracted with ethyl acetate (3×30 mL). The combined organic layer was washed with brine, dried over Na$_2$SO$_4$ and concentrated under reduced pressure. The resulting crude product was purified using flash chromatography (silica gel, hexanes: ethyl acetate, 50:50) to afford the pure 1-(4-hydroxybenzoyl)-3-(4-methoxybenzoyl)benzene 16 (0.2 g, 0.60 mmol) as a white solid in a 30% yield; $^1$H NMR (500 MHz, Acetone-d$_6$): δ 9.19 (s, O$\underline{H}$), 7.89 (dt, J=2 Hz, 0.5 Hz, 1H, Ar$\underline{H}$), 7.85 (dd, J=7.5 Hz, 1.5 Hz, 2H, Ar$\underline{H}$), 7.72 (ddd, J=10.0 Hz, 5.0 Hz, 3.0 Hz, 2H, Ar$\underline{H}$), 7.66 (ddd, J=9.5 Hz, 5.0 Hz, 3.0 Hz, 2H, Ar$\underline{H}$), 7.59 (td, J=7.5 Hz, 0.5 Hz, 1H, Ar$\underline{H}$), 6.96 (ddd, J=9.5 Hz, 4.5 Hz, 2.5 Hz, 2H, Ar$\underline{H}$), 6.86 (ddd, J=9.5 Hz, 5.0 Hz, 3.0 Hz, 2H, Ar$\underline{H}$), 3.78 (s, 3H, OC$\underline{H_3}$); $^{13}$C NMR (125 MHz, Acetone-d$_6$): δ 193.70, 193.56, 163.61, 161.941, 138.58, 138.35, 132.62, 132.41, 132.30, 130.16, 129.67, 128.75, 128.56, 115.25, 113.78, 55.12.

1-(4-hydroxybenzoyl), 3-(4-methoxybenzoyl)benzene 16 (0.20 g, 0.602 mmol) was dissolved in anhydrous methanol (10 mL). The solution was heated at reflux for 15 min, and thiosemicarbazide (0.066 g, 0.725 mmol) and a catalytic amount of p-toluenesulfonic acid were added. After 12 h at reflux, the solvent was removed under reduced pressure. Purification using flash chromatography (silica gel, hexanes:ethyl acetate, 60:40) afforded the desired a mixture of mono-thiosemicarbazone compounds 17 and 18 (0.01 g, 0.0247 mmol, 4% yield) and di-thiosemicarbazone compound 19 (0.015 g, 0.0314 mmol, 5.2% yield), both as a light yellow solid.

Compounds 17 and 18: HRMS (ESI) calculated for C$_{22}$H$_{19}$N$_3$O$_3$SH$^+$ (M+H) 406.1220, found 406.1221; compound 19: HRMS (ESI) calculated for C$_{23}$H$_{22}$N$_6$O$_2$S$_2$H$^+$ (M+H) 479.1318, found 479.1319. Compounds 17, 18 and 19: HPLC retention time 8.247, 8.454, 8.586, 8.752 min. The mixture of compounds 17, 18 and 19 was collected as two fractions from the same reaction. Fraction 2 is believed to be more pure than fraction 1, based upon preliminary LC-MS. Further, it is likely that compounds 17, 18 and 19 are present in different abundances in fractions 1 and 2. Both fractions were submitted for biological testing.

J. 1,3-bis-(4-isopropoxybenzoyl)benzene thiosemicarbazone (22)

To a well-stirred solution of 1,3-bis-(4-methoxybenzoyl)benzene 14 (1.80 g, 5.2 mmol) in dichloromethane (85 mL) was added boron trifluoride dimethyl sulfide complex (BF$_3$.SMe$_2$, 15 mL). The mixture was stirred for 27 h. After the reaction was quenched by water, the mixture was extracted with ethyl acetate (3×80 mL). The combined organic layer was washed with brine, dried over Na$_2$SO$_4$, and concentrated under vacuum. The resulting solid was further purified using flash chromatography (silica gel, hexanes: ethyl acetate, 50:50) to afford the pure 1,3-bis-(4-hydroxybenzoyl)benzene 20 (0.62 g, 1.95 mmol) as a white solid in a 38% yield; $^1$H NMR (500 MHz, Acetone-d$_6$): δ 9.28 (s, OH), 8.04 (td, J=1.7 Hz, 1.3 Hz, 1H, Ar$\underline{H}$), 7.98 (dd, J=7.7 Hz, 1.75 Hz, 2H, Ar$\underline{H}$), 7.80 (ddd, J=9.5 Hz, 4.8 Hz, 2.75 Hz, 4H, Ar$\underline{H}$), 7.73 (td, J=7.9 Hz, 0.45 Hz, 1H, Ar$\underline{H}$), 7.00 (ddd, J=9.5 Hz, 4.8 Hz, 2.75 Hz, 4H, Ar$\underline{H}$).

Reactions were conducted using a commercially available microwave reactor (Biotage). In a microwave vial, 1,3-bis-(4-hydroxybenzoyl)benzene 20 (0.310 g, 0.975 mmol), isopropyl bromide (0.851 g, 6.92 mmol) and potassium carbonate (0.955 g, 6.91 mmol) were added to DMF (10 mL), with a magnetic stir bar. The vial was capped tightly and the reaction mixture was heated from r.t. to 90° C. for 2 h. After the reaction mixture was cooled to room temperature, the vial was opened and the mixture was transferred to a round bottom flask. The mixture was quenched with water (50 mL) and extracted with ether (2×50 mL). The organic layer was washed with brine, dried over Na$_2$SO$_4$, and concentrated under reduced pressure. The crude product was purified using flash chromatography (silica gel, hexanes:ethyl acetate, 50:50) to afford the pure 1,3-bis-(4-isopropoxybenzoyl)benzene 21 (0.23 g, 0.57 mmol) as a white solid in a 59% yield; $^1$H NMR (500 MHz, Acetone-d$_6$): δ 8.07 (t, J=1.95 Hz, 1H, Ar$\underline{H}$), 7.99 (dd, J=7.6 Hz, 1.8 Hz, 2H, Ar$\underline{H}$), 7.84 (ddd, J=9.6 Hz, 5.2 Hz, 3.0 Hz, 4H, Ar$\underline{H}$), 7.71 (td, J=8.0 Hz, 0.25 Hz, 1H, Ar$\underline{H}$), 7.05 (ddd, J=10.1 Hz, 5.3 Hz, 3.2 Hz, 4H, Ar$\underline{H}$), 4.76 (Septet, J=6.05 Hz, 2H, C$\underline{H}$(CH$_3$)$_2$), 1.35 (d, J=6.05 Hz, 12H, CH(C$\underline{H_3}$)$_2$); $^{13}$C NMR (125 MHz, Acetone-d$_6$): δ 205.23, 193.51, 162.03, 138.41, 132.40, 130.25, 129.22, 128.57, 115.07, 69.96, 21.33.

1,3-bis-(4-isopropoxybenzoyl)benzene 21 (0.14 g, 0.39 mmol) was dissolved in anhydrous methanol (20 mL). The solution was heated at reflux for 15 min, and thiosemicarbazide (0.043 g, 0.47 mmol) and a catalytic amount of p-toluenesulfonic acid were added. After 10 h at reflux, the solvent was removed under vacuum and the resulting solid was further purified using flash chromatography (silica gel, hexanes:

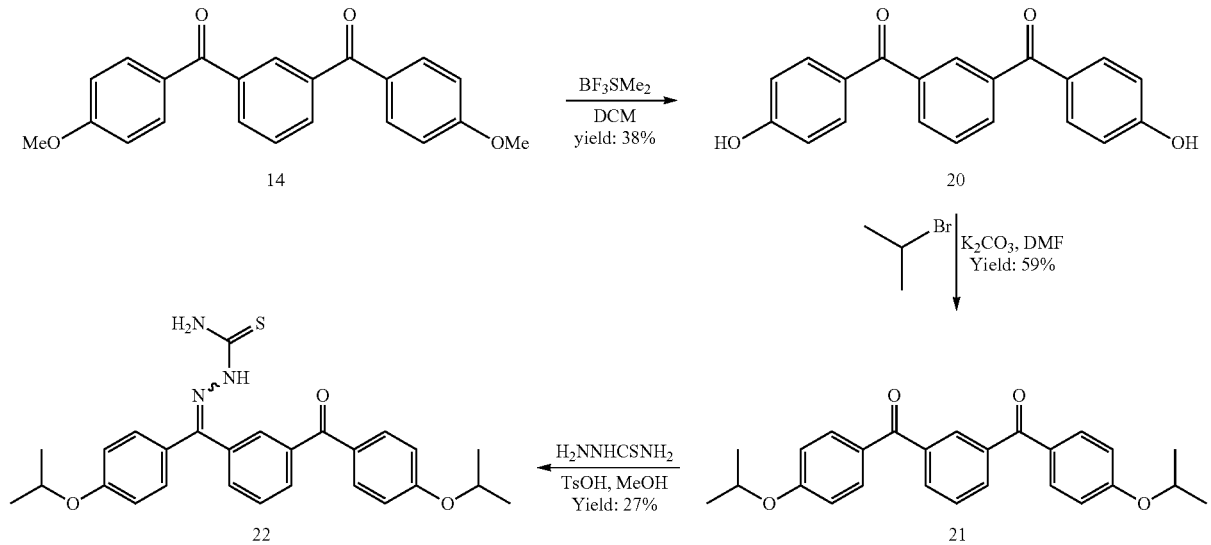

ethyl acetate, 50:50) to afford the desired 1,3-bis-(4-isopropoxybenzoyl)benzene thiosemicarbazone 22 as a white solid (0.05 g, 0.105 mmol, 27% yield); HRMS (ESI) calculated for $C_{27}H_{29}N_3O_3SH^+$ (M+H) 476.2002, found 476.2005; HPLC retention time 18.440, 18.767 min.

K. 1,3-bis-(4-isopropoxybenzoyl)benzene dithiosemicarbazone (23)

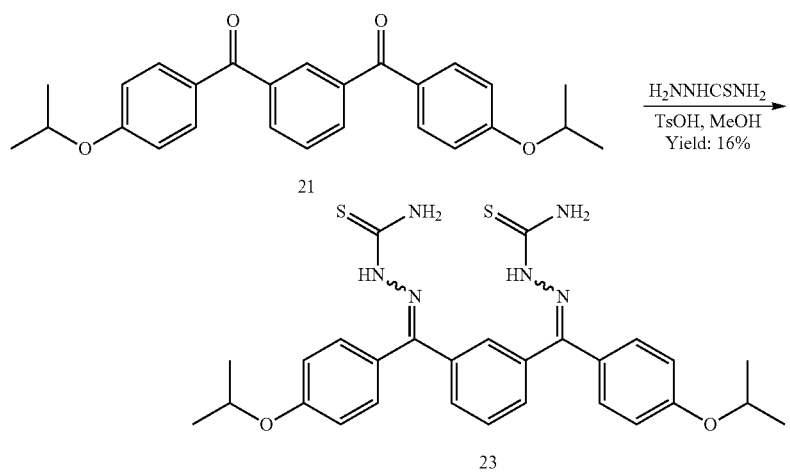

1,3-bis-(4-isopropoxybenzoyl)benzene 21 (0.092 g, 0.255 mmol) was dissolved in anhydrous methanol (12 mL). The solution was heated at reflux for 15 min, and thiosemicarbazide (0.019 g, 0.21 mmol) and a catalytic amount of p-toluenesulfonic acid were added. After 8 h at reflux, the solvent was removed under vacuum and the resulting solid was further purified using flash chromatography to (silica gel, hexanes:ethyl acetate, 50:50) afford the desired 1,3-bis-(4-isopropoxybenzoyl)benzene dithiosemicarbazone 23 as a light yellow solid (0.02 g, 0.042 mmol, 16% yield); HRMS (ESI) calculated for $C_{28}H_{32}N_6O_2S_2H^+$ (M+H) 549.2101, found 549.2103; HPLC retention time 10.788, 11.355, 11.525 min.

L. 1,3-bis-(4-bromobenzoyl)benzene thiosemicarbazone (24)

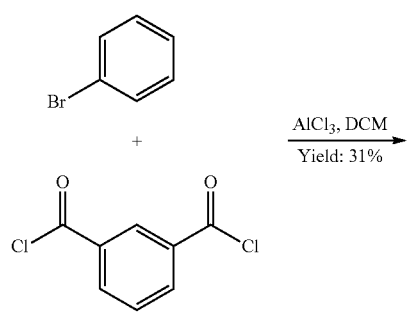

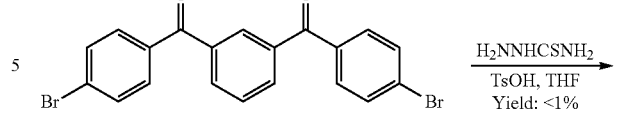

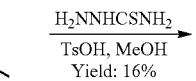

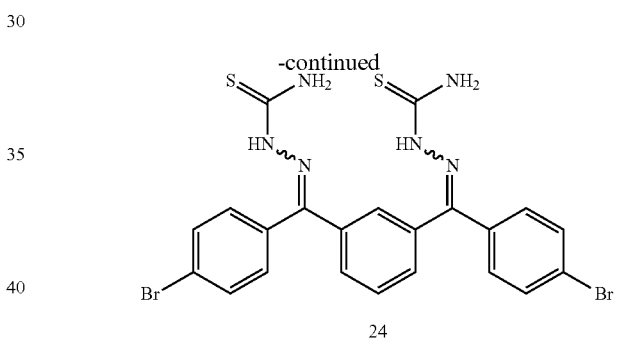

To a flask containing aluminum trichloride (1.36 g, 10.2 mmol) under nitrogen was added bromobenzene (15 mL, 142.8 mmol). Isophthalylchloride (1.00 g, 4.88 mmol) was dissolved in a minimal amount of bromobenzaldehyde and added to the reaction flask via syringe. The reaction stirred at reflux for 6 h, after which it was stirred at room temperature for 12 h, followed by another 3 h at reflux. The reaction was quenched with $H_2O$ (20 mL). The resulting mixture was then added to 50 mL of 10% HCl cooled in an ice bath. The mixture was extracted with ethyl acetate (3×10 mL) and the combined organic layers were washed sequentially with deionized water, dilute HCl, deionized water, and brine. Crude product crashed out of the organic layers as a white solid and was collected via filtration. Recrystallization of the solid from ethyl acetate afforded 1,3-bis-(4-bromobenzoyl)benzene 23. in 31% yield. $^1H$ NMR (DMSO-$d_6$, 500 MHz) δ 8.14-8.13 (m, 1H, ArH), 7.95 (dd, J=7.5 Hz, 1.5 Hz, 2H, ArH), 7.70-7.64 (m, 9H, ArH).

1,3-bis-(4-bromobenzoyl)benzene 23 (0.550 g, 1.21 mmol) was dissolved in dry THF (20 mL). The solution was heated at reflux for 15 min, and thiosemicarbazide (0.220 g, 2.42 mmol) and a catalytic amount of p-toluenesulfonic acid (0.023 g, 0.121 mmol) were added. After 24 h at reflux, the result solution was concentrated under reduced pressure and the residue was dissolved in dichloromethane (25 mL). The organic layer was washed with deionized water (15 mL), dried over $Na_2SO_4$, and concentrated. The crude product was purified via column chromatography to give the double condensation product 24 in <1% yield (6.7 mg, 11.3 μmol). Only the double condensation product was able to be isolated. $^1$H NMR (DMSO-$d_6$, 500 MHz) δ 9.87 (2H, bs, NH), 8.46 (2H, brs, NH), 8.29 (2H, brs, NH), 7.84 (1H, t, J=7.5 Hz, ArH), 7.64 (4H, d, J=8.5 Hz, ArH), 7.56 (4H, d, J=7.5 Hz, ArH), 7.48 (2H, dd, J=7.5 Hz, 1.5 Hz, ArH), 7.20 (1H, s, ArH). HRMS (ESI) calculated for $C_{22}H_{18}Br_2N_6S_2H^+$ $(M+H)^+$ 588.9474, found 588.9461.

M. 1,3,5-Tribenzoyl benzene thiosemicarbazone (25)

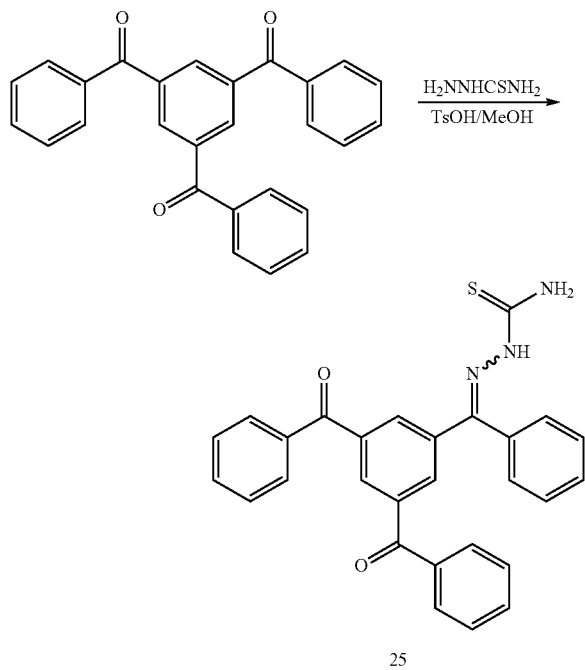

25

To a round bottom flask containing methanol (16 mL) was added 1,3,5-tribenzoylbenzene (0.250 g, 0.640 mmol). This was stirred under nitrogen and heated to reflux. Thiosemicarbazide (0.05536 g, 0.608 mmol) was then added to the flask, followed by p-toluenesulfonic acid (0.00122 g, 0.0064 mmol). The reaction mixture was stirred at reflux for 14 h. The crude mixture was purified using column chromatography, eluting with 35% ethyl acetate in hexanes, however the product still contained impurities and was submitted for testing without further purification. HRMS (ESI) calculated for $C_{28}H_{21}O_2N_3SH^+$ $(M+H)^+$ 464.14272, found 464.14267. Compound 25 was estimated to be approximately 80% pure by NMR, and was submitted for biological testing without further purification.

N. Biological Activity

Human liver Cathepsin L (Sigma) was preincubated with test compounds at various concentrations for 5 minutes at 25° C. The assay was initiated by addition of substrate Z-Phe-Arg-aminomethylcoumarin ("Z-F-R-AMC" Bacchem) and the final assay conditions were 1 nM cathepsin L, 50 μM Z-F-R-AMC, 100 mM sodium acetate pH 5.5, 1 mM EDTA (Omnipure), 3 mM DTT (EMD), 0.01% BRIJ 35 (Sigma), and 2.0% DMSO (Acros). Test compounds were serially diluted with DMSO and water to include a final concentration range of 10 μM to 10 pM. The reaction was monitored fluorometrically for 5 minutes at 25° C. using black 96-well Corning 3686 assay microplates with a Thermo Fluoroskan Ascent FL microplate reader at excitation and emission filter wavelengths of 355 nm and 460 nm, respectively. Data were analyzed to determine $IC_{50}$ values utilizing GraphPad Prism 4.03 software with a minimum of a triplicate on the same microplate.

Recombinant human procathepsin K was obtained from Enzo Life Sciences. Activation of the proenzyme was performed in 32.5 mM sodium acetate pH 3.5, EDTA 1 mM, NaCl 500 mM, human procathepsin K 5.5 μM, at room temperature. Activation times were optimized and varied between 35 and 150 minutes. Cathepsin K was preincubated with test compounds at various concentrations for 5 minutes at 25° C. The assay was initiated by addition of substrate Z-Phe-Arg-aminomethylcoumarin ("Z-F-R-AMC" Bacchem) and the final assay conditions were 1.5 nM cathepsin K, 50 μM Z-F-R-AMC, 150 mM sodium acetate pH 5.5, 2.5 mM EDTA (Omnipure), 2.5 mM DTT (EMD), 0.01% BRIJ 35 (Sigma), and 4.0% DMSO (Acros). Test compounds were serially diluted with DMSO and water to include a final concentration range of 10 μM to 10 pM. The reaction was monitored fluorometrically for 5 minutes at 25° C. using black 96-well Corning 3686 assay microplates with a Thermo Fluoroskan Ascent FL microplate reader at excitation and emission filter wavelengths of 355 nm and 460 nm, respectively. Data were analyzed to determine $IC_{50}$ values utilizing GraphPad Prism 4.03 software with a minimum of a triplicate on the same microplate.

Human liver Cathepsin B (Calbiochem) was pre-incubated with test compound at various concentrations for 5 minutes at 37° C. The assay was initiated by addition of substrate Z-Arg-Arg-aminomethylcoumarin ("Z-R-R-AMC" Bacchem) and the final assay conditions were 1.1 nM cathepsin B, 60 μM Z-R-R-AMC, 126 mM sodium potassium phosphate pH 6.0 (Fisher), 0.3 mM EDTA (Omnipure), 2.7 mM DTT (Omnipure), 0.004% BRIJ 35 (Sigma), and 2.0% DMSO (Acros) in a final volume of 200 μL. Test compounds were serially diluted with DMSO and 0.01% BRIJ 35 to include a final concentration range of 20 μM to 10 pM. The reaction was monitored fluorometrically for 5 minutes at 37° C. using black 96-well Corning 3686 assay microplates with a Thermo Fluoroskan Ascent FL microplate reader at excitation and emission filter wavelengths of 355 nm and 460 nm, respectively. Data were analyzed to determine IC50 values utilizing GraphPad Prism 4.03 software with a minimum of a triplicate on the same microplate.

TABLE 4

| | Biological Activity | | |
| --- | --- | --- | --- |
| | $IC_{50}$ | | |
| Compound | Cathepsin L (nM) | Cathepsin K (nM) | Cathepsin B (nM) |
| 3 | 10.5 | 17.4 | >10,000 |
| 6 | 23.8 | nd | >10,000 |
| 9 | 7,823 | 1,034 | nd |
| 11 | 8.12 | nd | >10,000 |
| 13 | 24.3 | 8,500 | >10,000 |
| 17, 18 & 19 (fraction 1) | >10,000 | 6,162 | >10,000 |

TABLE 4-continued

| Compound | Biological Activity IC$_{50}$ | | |
|---|---|---|---|
| | Cathepsin L (nM) | Cathepsin K (nM) | Cathepsin B (nM) |
| 17, 18 & 19 (fraction 2) | >10,000 | 3,204 | >10,000 |
| 22 | >10,000 | nd | >10,000 |
| 23 | >10,000 | >10,000 | nd |
| 24 | >10,000 | >10,000 | >10,000 |
| 25 | 25.0 | 2,796 | nd |
| 33 | 587 | 2,105 | >10,000 |

We claim:

1. A compound of formula I:

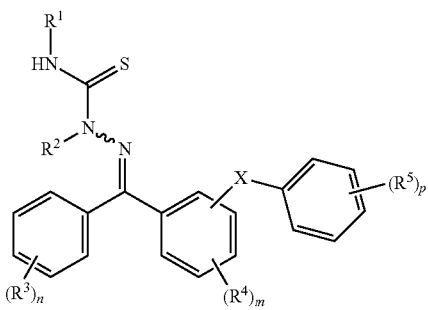

I or a solvate or pharmaceutically acceptable salt thereof, wherein

X is selected from the group consisting of C(=O), CH(OR$^6$) and

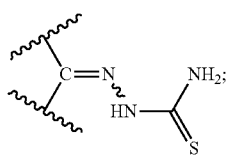

n is 0, 1, 2 or 3;
m is 0, 1, 2 or 3;
p is 0, 1, 2 or 3;
R$^1$ is hydrogen, C$_1$-C$_3$ alkyl, aryl and arylalkyl;
R$^2$ is hydrogen or C$_1$-C$_3$ alkyl;
each R$^3$ and R$^5$ independently is selected from the group consisting of hydroxyl, C$_1$-C$_3$ alkyl, C$_1$-C$_2$ alkoxy, fluoro, and chloro;
each R$^4$ independently is selected from the group consisting of hydroxyl, C$_1$-C$_6$ alkyl, C$_1$-C$_6$ alkoxy, halo, amino, nitro, nitroso and acyl; and
R$^6$ is selected from the group consisting of hydrogen and methyl.

2. The compound of claim 1, wherein X is C(=O) or CH(OR$^6$).
3. The compound of claim 2, wherein X is C(=O).
4. The compound of claim 1, wherein m is zero.
5. The compound of claim 4, wherein n is zero and p is zero.
6. The compound of claim 1, wherein n is zero and p is zero.
7. The compound of claim 1 wherein m is 1.
8. The compound of claim 7, wherein R$^4$ is halo or acyl.
9. The compound of claim 8, wherein R$^4$ is substituted aryl-C(O)— or unsubstituted aryl-C(O)—.
10. The compound of claim 8, wherein R$^4$ is benzoyl.
11. The compound of claim 1, wherein
each of n and p, independently, is zero or one; and
each of R$^3$ and R$^5$, independently, is selected from the group consisting of hydroxyl, methyl, methoxy and fluoro.
12. The compound of claim 1, having formula II, or a solvate or pharmaceutically acceptable salt thereof:

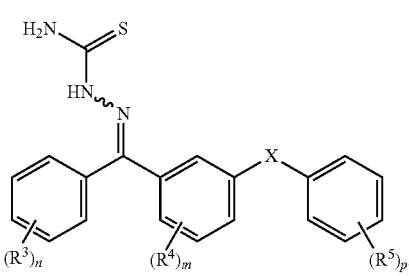

II

13. The compound of claim 12, wherein X is C(=O).
14. The compound of claim 13, wherein each of n, m and p, independently, is zero or one.
15. The compound of claim 13, wherein n is one and R$^3$ is selected from the group consisting of hydroxyl, methyl, methoxy, and fluoro.
16. The compound of claim 13, wherein p is one and R$^5$ is selected from the group consisting of hydroxyl, methyl, methoxy and fluoro.
17. The compound of claim 13, wherein m is one and R$^4$ is selected from the group consisting of halo and acyl.
18. The compound of claim 12, wherein X is

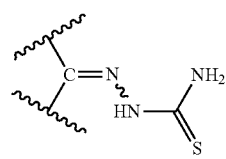 [SMILES: *C(*)=NNC(N)=S]

and m is zero or one.
19. The compound of claim 18, wherein each of n and p, independently, is zero or one.
20. The compound of claim 1, having formula III, or a solvate or pharmaceutically acceptable salt thereof:

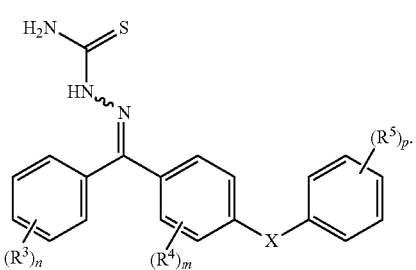

III

* * * * *